United States Patent
Mansour et al.

(10) Patent No.: US 12,042,537 B2
(45) Date of Patent: *Jul. 23, 2024

(54) METHODS OF USING LOW DOSE VOLUME B-CELL EPITOPE COMPOSITIONS FOR INDUCING AN ANTIBODY IMMUNE RESPONSE IN HUMAN SUBJECTS

(71) Applicant: BioVaxys Inc., New York, NY (US)

(72) Inventors: Marc Mansour, Halifax (CA); Frederic Ors, Quebec (CA); Marianne Stanford, Upper Tantallon (CA); Leeladhar Sammatur, Irvine, CA (US); Rajkannan Rajagopalan, Dartmouth (CA); Lisa Diana MacDonald, Halifax (CA)

(73) Assignee: BioVaxys Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,205

(22) Filed: Jun. 30, 2022

(65) Prior Publication Data

US 2022/0347296 A1    Nov. 3, 2022

Related U.S. Application Data

(63) Continuation of application No. 16/336,162, filed as application No. PCT/CA2016/051127 on Sep. 27, 2016, now Pat. No. 11,406,705.

(51) Int. Cl.
| | | |
|---|---|---|
| *C12N 7/00* | (2006.01) | |
| *A61K 39/07* | (2006.01) | |
| *A61K 39/12* | (2006.01) | |
| *A61K 39/39* | (2006.01) | |
| *A61P 31/14* | (2006.01) | |
| *A61P 35/00* | (2006.01) | |
| *A61P 37/04* | (2006.01) | |
| *C07K 14/775* | (2006.01) | |
| *A61K 39/00* | (2006.01) | |

(52) U.S. Cl.
CPC .............. *A61K 39/39* (2013.01); *A61K 39/12* (2013.01); *A61P 31/14* (2018.01); *A61P 37/04* (2018.01); *C07K 14/775* (2013.01); *C12N 7/00* (2013.01); *A61K 2039/54* (2013.01); *A61K 2039/55505* (2013.01); *A61K 2039/55516* (2013.01); *A61K 2039/55566* (2013.01); *A61K 2039/55572* (2013.01); *A61K 2039/575* (2013.01); *A61K 2039/6018* (2013.01); *A61K 2039/6031* (2013.01); *C07K 2319/33* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | |
|---|---|---|---|
| 6,090,406 A | 7/2000 | Popescu et al. | |
| 9,409,973 B2 | 8/2016 | Saelens et al. | |
| 9,498,493 B2 | 11/2016 | Mansour et al. | |
| 9,925,142 B2 | 3/2018 | Daftarian et al. | |
| 10,105,435 B2 | 10/2018 | Mansour et al. | |
| 10,117,926 B2 * | 11/2018 | Saelens ................. | A61P 31/12 |
| 10,232,052 B2 | 3/2019 | Mansour et al. | |
| 10,272,042 B2 | 4/2019 | Daftarian et al. | |
| 11,406,705 B2 * | 8/2022 | Mansour ................ | A61K 39/12 |
| 2004/0133160 A1 | 7/2004 | Dalton | |
| 2015/0359863 A1 | 12/2015 | Ballou, Jr. et al. | |
| 2019/0290743 A1 | 9/2019 | Mansour et al. | |

FOREIGN PATENT DOCUMENTS

| | | |
|---|---|---|
| JP | 2009-520761 A | 5/2009 |
| JP | 2016-516755 A | 6/2016 |
| WO | 2009/043165 A1 | 4/2009 |
| WO | 2013/049941 A1 | 4/2013 |
| WO | 2013/116965 A1 | 8/2013 |
| WO | 2014/153636 A1 | 10/2014 |
| WO | 2016/176761 A1 | 11/2016 |

OTHER PUBLICATIONS

European Search Report issued in corresponding EP Application No. 16917017.2 on May 12, 2020.
Levie et al., "An adjuvanted, low-dose, pandemic influenza A (H5N1) vaccine candidate in safe, immunogenic, and induces cross-reactive immune responses in healthy adults", Journal of Infectious Diseases, vol. 198, No. 5, Sep. 1, 2008, pp. 642-649.
International Preliminary Report of Patentability and Written Opinion dated Apr. 2, 2019 issued in International Application No. PCT/CA2016/051127 by the International Searching Authority.
International Search Report for PCT/CA2016/051127 mailed Jun. 22, 2017.
Caproni et al., "MF59 and Pam3CSK4 Boost Adaptive Responses to Influeneza Subunit Vaccine through an IFN Type I-Independent Mechanism of Action", The Journal of Immunology, 2012, vol. 188, pp. 3088-3098.
Spohn et al., "Synthetic lipopeptide adjuvants and Toll-like receptor 2-structure-activity relationships", Vaccine, 2004, vol. 22, pp. 2494-2499.
Varypataki et al., "Synthetic long peptide-based vaccine formulations for induction of cell mediated immunity: A compartive study of cationic lipsomes and PLGA nanoparticles", Journal of Controlled Release, Feb. 2016, vol. 226, pp. 98-106.

(Continued)

*Primary Examiner* — Agnieszka Boesen
(74) *Attorney, Agent, or Firm* — Troutman Pepper Hamilton Sanders LLP

(57) ABSTRACT

The present disclosure provides methods, uses and compositions and kits for use in inducing an antibody immune response in a human subject. The methods and uses involve administering parenterally a low dose volume of a composition comprising an antigen comprising a B-cell epitope, an amphipathic compound, and a hydrophobic carrier, wherein the low dose volume of the composition is less than 100 µl and induces an antibody immune response to the B-cell epitope in the human subject.

19 Claims, 3 Drawing Sheets

Specification includes a Sequence Listing.

(56) References Cited

OTHER PUBLICATIONS

Hanson et al., "Liposomal vaccines incorporating molecular adjuvants and instrastructural T-cell help promote the immunogenicity of HIV membrane-proximal external region peptides", Vaccine, 2015, vol. 33, pp. 861-868.
Office Action issued in JP Application No. 2019-516487 mailed on Nov. 4, 2020.
Kishishita et al., Pharmacology, Jul. 2016, vol. 76, No. 1, pp. 46-50. (cited in JP Office Action issued in JP Application No. 2022-077537, dated Jun. 27, 2023).
Wilson-Welder et al., "Vaccine Adjuvants: Current Challenges and Future Approaches", Journal of Pharmaceutical Sciences, 2009, vol. 98, No. 4, pp. 1278-1316.
Office Action Issued in JP Application No. 2022-077537, dated Jun. 27, 2023.

\* cited by examiner

METHODS OF USING LOW DOSE VOLUME B-CELL EPITOPE COMPOSITIONS FOR INDUCING AN ANTIBODY IMMUNE RESPONSE IN HUMAN SUBJECTS

CROSS-REFERENCE TO RELATED APPLICATIONS

This application is a continuation of U.S. application Ser. No. 16/336,162, filed Mar. 25, 2019, which is a U.S. National Phase of International Patent Application No. PCT/CA2016/051127, filed Sep. 27, 2016. Each of which are herein incorporated by reference in their entirety.

SEQUENCE LISTING

This application contains a Sequence Listing which has been submitted in ASCII format via EFS-Web and is hereby incorporated by reference herein in its entirety. The ASCII text file created on May 4, 2018, is named 249979000152SEQLIST.txt and is 5,173 bytes in size.

FIELD

The present invention relates generally to methods for inducing an antibody immune response in a human subject by parenterally administering a low dose volume of a composition comprising an antigen comprising a B-cell epitope, an amphipathic compound, and a hydrophobic carrier.

BACKGROUND

B-cell epitopes are fragments of, for example, a protein that are recognized by an antibody produced by B-cells. Continuous B-cell epitopes, such as linear segments of a protein, can be used as antigens in subunit vaccines to induce antibody responses. However, continuous B-cell epitopes have had limited success in development. This may be partially due to ineffective delivery of antigen to the immune system.

Among the currently approved vaccines in Canada, based on 2016 Centers for Disease Control and Prevention (CDC) recommendations (CDC website—Advisory Committee for Immunization Practices (ACIP) Vaccine Recommendations) for adults 65 years and older, that are administered via the intramuscular route, the range of dose volume is 0.5 mL to 1.0 mL. The smallest dose volume of an approved vaccine is 0.1 mL for Fluzone Intradermal Quadrivalent (Sanofi Pasteur); however, only for adults between 18-64 years and administered via the intradermal route.

In the present disclosure, we report novel methods for inducing an antibody immune response in a human subject using low dose volumes of a parenterally administered composition comprising an antigen comprising a B-cell epitope, an amphipathic compound, and a hydrophobic carrier.

SUMMARY

In an embodiment, the present disclosure relates to a method for inducing an antibody immune response in a human subject, comprising administering parenterally to the human subject a low dose volume of a composition comprising: an antigen comprising a B-cell epitope; an amphipathic compound; and a hydrophobic carrier, wherein the low dose volume of the composition is less than 100 µl and induces an antibody immune response to the B-cell epitope in the human subject.

In an embodiment, the present disclosure relates to the use of a low dose volume of a composition comprising: an antigen comprising a B-cell epitope; an amphipathic compound; and a hydrophobic carrier, for inducing an antibody immune response to the B-cell epitope in a human subject, wherein the composition is for administration parenterally and the low dose volume of the composition is less than 100 µl.

In an embodiment of the methods and uses disclosed herein, the low dose volume for parenteral administration is about 50 µl. In an embodiment, the parenteral administration is an intramuscular injection.

In an embodiment of the methods and uses disclosed herein, the antigen comprises or consists of the ectodomain of the small hydrophobic protein (SH) of a subgroup A human RSV strain or a subgroup B human RSV strain. In an embodiment, the antigen comprises or consists of the amino acid sequence NKLCEYNVFHNKTFELPRARVNT (SEQ ID NO: 1), NKLSEHKTFCNKTLEQGQMYQINT (SEQ ID NO: 2), or a fragment thereof.

In an embodiment of the methods and uses disclosed herein, the amphipathic compound is a lipid or a lipid mixture. In an embodiment, the amphipathic compound is a lipid mixture of dioleoyl phosphatidylcholine (DOPC) and cholesterol.

In an embodiment of the methods and uses disclosed herein, the hydrophobic carrier is mineral oil or is a mannideoleate in mineral oil solution, for example Montanide® ISA 51 VG.

In an embodiment of the methods and uses disclosed herein, the composition comprises: a peptide comprising the amino acid sequence NKLCEYNVFHNKTFELPRARVNT (SEQ ID NO: 1); a lipid mixture comprising dioleoylphosphatidylcholine (DOPC) and cholesterol; a short synthetic lipopeptide which is PAM$_3$Cys-Ser-(Lys)4 (SEQ ID NO: 3); and Montanide® ISA 51 VG In an embodiment of the methods and uses disclosed herein, the composition is water-free or substantially free of water.

Other aspects, embodiments and features of the present invention will become apparent to those of ordinary skill in the art upon review of the following description in conjunction with the accompanying claims and figures.

BRIEF DESCRIPTION OF THE FIGURES

In the figures, which illustrate embodiments of the invention by way of example only.

(A), 56 (B), and 84 (C). Subjects in the oil-based group received two vaccinations on study day 0 and 56. Subjects in the alum-based group received one vaccination on study day 0 and a placebo on study day 56. Subjects in the placebo group received placebo injections on study days 0 and 56. Results below the limit of detection are reported as log 10=0. Data shown for each individual subject (n=4-8), bar indicates average. Statistical significance calculated by student's t test comparing the oil-based formulation to the alum-based formulation: *p<0.05, ***P<0.001.

Figure 3:
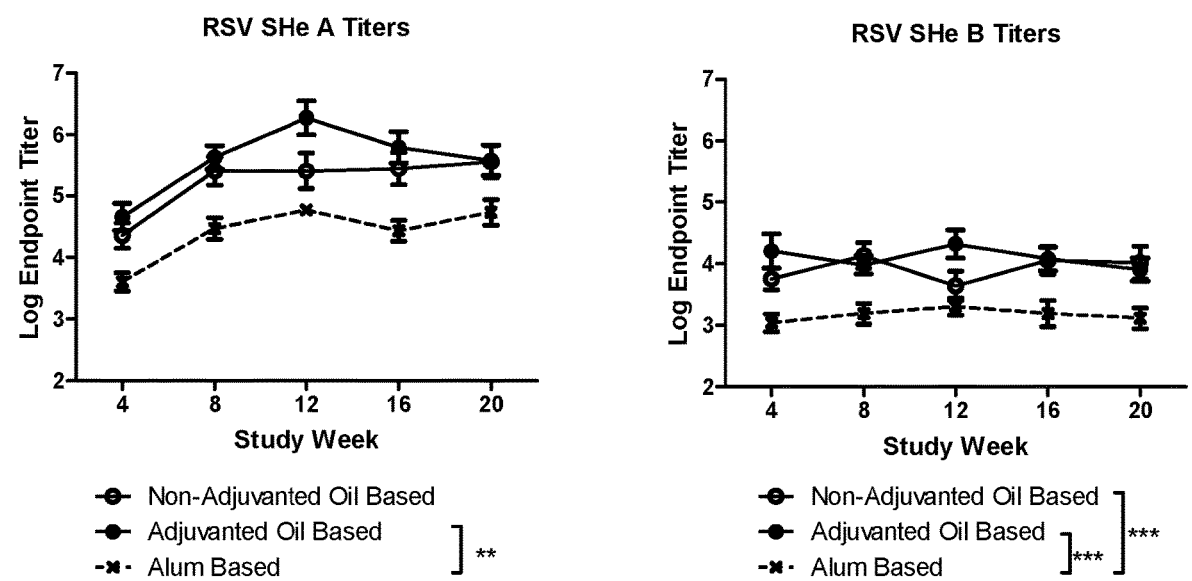

FIG. 3 shows RSV SHe A and RSV SHe B antibody titers induced in mice following vaccination with RSV SHe A peptide antigen and RSV SHe B peptide antigen formulated in a non-adjuvanted oil-based vaccine, an adjuvanted oil-based vaccine or an aqueous-based vaccine. Mice in each group were vaccinated on study days 0 and 28 and bled every four weeks for serum antibody detection by ELISA. Statistical significance by 1-way ANOVA with Tukey post test: $p<0.01$, $*p<0.001$.

DETAILED DESCRIPTION

Inducing strong and effective antibody immune responses in a human subject against an administered synthetic linear B-cell epitope is difficult and often requires multiple immunizations with typical dose volumes of 0.5 mL to 1.0 mL. Even then, immunizations using compositions comprising B-cell epitopes have often been unsuccessful in human subjects, with pre-clinical studies not being overly predictive of success in humans. Indeed, there has been limited success in development of vaccine compositions to continuous B-cell epitopes.

Previously, we have demonstrated that a dose volume of 0.1 mL of a DepoVax-based vaccine, in combination with cyclophosphamide, can be used to elicit a cellular immune response (mediated by $CD8^+$ T cells) to peptide antigens. However, these findings which relate to combination therapeutics and a different arm of the immune system (cellular immune responses) do not provide any teaching or suggestion of the presently disclosed methods using even lower dose volumes to induce a humoral immune response (mediated by B-cells) against B-cell epitopes.

The present disclosure provides methods for inducing an antibody immune response in a human subject. Surprisingly, the present inventors have found that a composition comprising an antigen comprising a B-cell epitope, an amphipathic compound and a hydrophobic carrier can be administered parenterally at a low dose volume and provide a strong and effective antibody immune response in a human subject. This result has been demonstrated in human clinical trials.

As shown in the examples herein, the methods disclosed herein using low dose volumes are capable of inducing antigen-specific antibody immune responses in 100% of subjects vaccinated with a low peptide (10 μg antigen) or a high peptide (25 μg antigen) oil-based composition described herein by Day 236 and Day 84, respectively (FIGS. 1 and 2). The dose volume for the compositions was only 50 μl. With such a low dose volume, it is surprising that the human subjects were able to generate an antibody immune response at all, let alone to such an extent as in 100% of subjects.

Moreover, the Day 56 results demonstrate that the methods disclosed herein are capable of inducing antigen-specific antibody immune responses in 50% and 62.5% of subjects vaccinated with a low peptide (10 μg antigen) and high peptide (25 μg antigen) oil-based composition as described herein, respectively (FIGS. 1 and 2). In contrast, human subjects vaccinated with an aqueous alum composition generally did not induce a detectable antibody immune response at all, with only 25% of low peptide subjects and 12.5% of high peptide subjects exhibiting a detectable antibody immune response. Thus, the number of subjects having a detectable antibody immune response was 2.0 times higher with the low peptide compositions described herein and 5.0 times higher with the high peptide compositions described herein, as compared to the alum compositions.

In addition to the increased number of human subjects demonstrating a detectable antibody immune response by the methods disclosed herein, the antibody titers obtained were also significantly higher using the disclosed methods and compositions, as compared to using aqueous alum compositions. As shown in Table 1, the average endpoint titer with a low peptide (10 μg antigen) oil-based composition described herein was about 123.2 times higher at Day 28 and about 16.7 times higher at Day 56 than with the alum compositions. For the high peptide (25 μg antigen) oil-based composition described herein, the average endpoint titer was about 35.3 times higher at Day 28 and about 13.1 times higher at Day 56 than with the alum compositions. This increase in antibody titer was observed with only a single administration of the compositions. This level of enhancement in human subjects is surprising and unexpected.

The results in the examples further demonstrate that the methods disclosed herein are capable of inducing strong antibody immune responses in human subjects at least as early as 28 days after a single administration, and that the antibody immune response can persist for a prolonged period of time. For example, with only two administrations (Day 0 and Day 56), high levels of antibody titers still persisted at least until Days 84 and 236. (FIGS. 1 and 2; Table 1). The ability of the disclosed methods to induce an antibody immune response that persists for this length of time with only two low dose volume administrations of the composition is a surprising result.

Overall, the results show that low dose volumes of an aqueous alum composition were generally ineffective in inducing strong antibody immune responses in a sufficient number of human subjects. Surprisingly however, low dose volumes of a composition comprising an antigen comprising a B-cell epitope, an amphipathic compound, and a hydrophobic carrier induced strong antibody immune responses in most (low peptide) or all (high peptide) of the human subjects. Without being bound by theory, this may be due to one or more of: the nanoparticulate drug delivery system having potentially solved some of the formulation issues related to antigen solubility; controlled and sustained release properties of the compositions disclosed herein; overcoming poor bioavailability; smaller drug doses; decreased dosing variability; increase antigen stability at the site of injection; increased resistance to unspecific degradation etc.

The clinical study results also show that the low dose volumes of the compositions disclosed herein were well tolerated and had an acceptable safety profile. As used herein, by "acceptable safety profile" it is meant at least that there were no reports of any serious adverse events. As described in Example 1, no serious adverse events were reported among all study participants.

As used herein, a "serious adverse event" (SAE) is an untoward medical occurrence that results in death, is life-threatening (that is, there was a risk of death at the time of the event), requires hospitalization or prolongation of existing hospitalization, results in disability/incapacity, or is a congenital anomaly/birth defect in the offspring of a study subject.

As discussed in Example 1, the most common solicited local adverse event reported was mild injection site pain. It is believed that this level of injection site reaction would not require any sort of pain management. Moreover, no increase in injection site pain was observed with the delivery of the booster dose of the oil-based composition.

The most common solicited systemic adverse events reported were drowsiness, nausea, diarrhea and muscle aches. For total unsolicited adverse events, there were no serious adverse events reported and all other events recovered or resolved.

As used herein, the term "solicited adverse event" is a pre-specified outcome that the participant in the clinical trial is asked to record as present or not, and if present, to apply an intensity rating. Solicited adverse events were collected daily from days 0 to 6 following administration of the study vaccine. The following local (injection-site) adverse events were solicited: pain at injection site; redness at injection site and swelling at injection site. The following general (systemic) adverse events were solicited: drowsiness; fever; nausea; diarrhea; vomiting; and generalized muscle aches.

As used herein, an unsolicited event is one that the participant in the clinical study identifies when asked in a non-leading manner if there have been any changes in their health since the last study visit. Unsolicited adverse events were collected during study visits after vaccine administration The results described herein are surprising and unexpected at least because it was known that vaccine compositions comprising B-cell epitopes often do not work at all to generate detectable antibody immune responses in human subjects. Also, larger volumes (e.g. 0.5 mL to 1.0 mL) were previously believed to be significant for parenterally administered compositions (e.g. intramuscular) in order to provide adequate systemic diffusion to effectively engage immune system components, such as for aqueous vaccines, and/or to attract immune system components to the site of injection, such as for oil-based vaccines.

Embodiments of the methods and compositions disclosed herein will be described in greater detail in the sections that follow.

Methods for Inducing an Antibody Response

In an embodiment, the present disclosure relates to a method for inducing an antibody immune response in a human subject, comprising administering parenterally to the human subject a low dose volume of a composition comprising: an antigen comprising a B-cell epitope; an amphipathic compound; and a hydrophobic carrier, wherein the low dose volume of the composition is less than 100 µl and induces an antibody immune response to the B-cell epitope in the human subject.

As used herein, "inducing" or "to induce" an antibody immune response is to generate, elicit, improve and/or potentiate an immune response. By "generate" or "elicit" it is meant that the human subject has not previously developed, and/or has no ongoing antibody immune response to the antigen, and the methods disclosed herein result in a detectable antibody immune response in the subject. By "improve" or "potentiate" it is meant that the antibody immune response is enhanced, elevated, or strengthened to the benefit of the subject relative to the prior immune response status, for example, before the application of the methods of the invention.

The term "detectable" as used herein in the context of a "detectable antibody immune response", means that an antigen-specific antibody immune response can be detected in the human subject, such as for example by analysis of a bodily fluid (e.g. whole blood, serum, etc.) or by medical therapeutic assessment of the subject. As an exemplary embodiment, a "detectable antibody immune response" is one in which antibody titer can be detected in samples of human serum from immunized subjects by enzyme-linked immunosorbent assay (ELISA) at a limit of detection of a 1/100 dilution, as described in the examples herein.

In some embodiments, "inducing" or "to induce" means that there is an improved efficacy in eliciting or generating an antibody immune response to the antigen. As used herein, "improved efficacy", "improving the efficacy" or the like refers to any change or alteration in the immune response of a subject that is capable of rendering the compositions more effective in treating a disease or disorder. In some embodiments, this may involve accelerating the appearance of an immune response and/or improving the persistence or strength of an immune response.

In some embodiments, "inducing" or "to induce" refers to the ability to generate, elicit, strengthen or prolong an antigen-specific recall response in a subject that has previously been primed by an earlier immunization or other exposure to the antigen. As opposed to a primed immune response that occurs upon first exposure to an antigen, a recall immune response is the immune response occurring on the second and/or subsequent exposures to an antigen, re-establishing an immune response that was previously produced by a prime immunization or other exposure to the antigen (e.g. prior pathogen infection).

In some embodiments, "inducing" or "potentiating" refers to the ability to maintain and/or boost an antigen-specific antibody immune response in a subject that has previously been primed by an earlier immunization or other exposure to the antigen. By "maintain and/or boost", it is meant that the previously induced immune response is enhanced, elevated, improved, strengthened or prolonged to the benefit of the subject.

As used herein, "potentiate" encompasses instances in which the antibody immune response to the antigen is made more effective or an adverse event is avoided, abolished or lessened in strength and/or duration. By "more effective", it is meant that the immune response is enhanced, elevated, improved, strengthened or prolonged to the benefit of the subject relative to the prior immune response status of the subject. In some embodiments, "potentiating" refers to the ability to reduce the occurrence of an adverse event. For example, in an embodiment, potentiating the immune response may involve a reduction in the occurrence of injection site reactions caused by larger dose volumes of the compositions described herein or different compositions.

The methods disclosed herein involve the use of a "low dose volume" of the composition administered parenterally to a human subject. As use herein, "low dose volume" refers to the total volume of the composition that is given to the human subject in a single administration. By "single administration" it is meant that the complete dose at a particular time point (e.g. Day 0) is given to the subject by a single parenteral injection or infusion.

The "low dose volume" is less than 100 µl of the composition described herein. In some embodiments, the low dose volume is about 50 µl, about 55 µl, about 60 µl, about 65 µl, about 70 µl, about 75 µl, about 80 µl, about 85 µl, about 90 µl or about 95 µl of the composition. In some embodiments, the low dose volume is between about 50 µl to about 75 µl of the composition. In some embodiments, the low dose volume is about 50 µl or exactly 50 µl. The low dose volume is a volume that is capable of inducing an antibody immune response in the human subject.

In contrast to "low dose volume", the term "dose" as used herein refers to the total amount or quantity (e.g. micrograms, milligrams, molar amount, etc.) of a vaccine component, such as for example antigen, contained within the low dose volume. The term "dose" may also be used herein interchangeably with "administration" to signify the action of administering the composition to the human subject.

By "parenteral administration" or "administering parenterally", it is meant that the composition is administered by injection or by infusion. In some embodiments, the route of administration may be intravenous, intra-muscular, subcutaneous, intraperitoneal, intrathecal, intra-arterial, intracerebroventricular, intracerebral, intraosseous, intradermal or intrapulmonary. In some embodiments, the administration is by injection and the route of administration is intravenous (IV), intra-muscular (IM) or subcutaneous (SC). In an embodiment, the parenteral administration is intramuscular injection.

It is within the ability of the skilled person to determine the number of low dose volume administrations, the interval between the administrations, and the total duration of the treatment or immune protocol. These features may, for example, be dependent upon the antigen used, the level of humoral immunity desired, the subject and/or the disease or disorder.

In some embodiments, a low dose volume administration of the composition is given to the human subject 1, 2, 3, 4, 5, 6, 7, 8, 9, 10 or more times over the course of a complete immunization protocol. In a more particular embodiment, the low dose volume of the composition is administered to the human subject only two times. For example, in an embodiment, the first time may be as a priming administration and the second time may be as a booster administration. As used herein, a "priming administration" refers to the first administration of the composition to the subject, which has the effect of presenting the antigen to the immune system. In contrast, a "booster administration" refers to a second or any subsequent re-introduction of the same antigen to the subject. While the antigen is the same in both the priming and booster administrations, in some embodiments other components of the compositions may be different.

The interval between administrations of the low dose volume of the compositions is within the ability of the skilled person. In an embodiment, the interval should be close together enough that a significant decline in the induction of the immune response does not occur. In some embodiments, after a first administration of the composition, each subsequent administration is within about 12 hours, about 1 day, about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, or more after the immediately preceding administration. In a more particular embodiment, each subsequent low dose volume administration is within about 4 weeks, about 8 weeks or about 12 weeks after the immediately preceding administration, and in a further embodiment it is at about 8 weeks (56 days) after the immediately preceding administration.

In an embodiment, the methods disclosed herein comprise administering only a single low dose volume priming administration and a single low dose volume booster administration of the composition. In an embodiment, the single booster administration is provided to the human subject about 56 days after the single priming administration.

In another embodiment, the methods disclosed herein comprise administering only a single low dose volume administration of the compositions disclosed herein.

The duration of time over which the composition may be administered, from first administration to last, is within the ability of the skilled person but should not be so long as to encounter adverse effects or events. In some embodiments, the duration of time from first to last administration is about 0 days (single administration embodiments), about 1 week, about 2 weeks, about 1 month, about 2 months, about 3 months, about 4 months, about 5 months, about 6 months, about 7 months, about 8 months, about 9 months, about 10 months, about 11 months, about 1 year or longer. In an embodiment, the duration of time is about 8 weeks (56 days).

In an embodiment, the methods disclosed herein may further comprise administering to the human subject, after at least one administration of the low dose volume of the composition described herein, a subsequent dose of the antigen formulated in an aqueous composition that does not comprise the hydrophobic carrier or does not comprise the hydrophobic carrier and the amphipathic compound. In an embodiment of these methods, the low dose volume compositions would be a "depot-forming vaccine" and the aqueous composition would be a "non-depot-forming vaccine". Exemplary methods and compositions are disclosed for example in International Patent Application No. PCT/CA2016/050487, which was filed on Apr. 27, 2016.

By "depot-forming vaccine", it is meant that upon administration to the human subject, the vaccine and its components (e.g. antigen, adjuvant, etc.) remain localized at the site of vaccine injection for a period of time, and are not rapidly dispersed throughout the body of the subject. This is referred to herein as a "depot effect", whereby a substantial release of the antigen, or the antigen and one or more other vaccine components, from the site of injection does not occur for a prolonged period of time. The period of time by which the antigen or the antigen and one or more other vaccine components remain at the site of injection may be dependent upon how the depot effect is achieved. As used herein, the term "depot-forming vaccine" broadly means that a substantial proportion of the antigen or the antigen and one or more other vaccine components are held at the site of injection for a longer period of time than if the antigen and other components were administered in a non-depot-forming vaccine.

By "non-depot-forming vaccine", it is meant that upon administration to the human subject, the vaccine and its components (e.g. antigen, adjuvant, etc.) are rapidly dispersed in the body of the subject and a "depot effect" is not obtained or does not persist. For a non-depot-forming vaccine, the antigen or the antigen and one or more other vaccine components are cleared from the site of injection substantially faster than the respective components of a depot-forming vaccine. Thus, the non-depot-forming vaccine rapidly re-exposes a previously primed immune system to the antigens and other vaccine components, and then dissipates from the site of injection. In an embodiment, greater than 50%, 60%, 70%, 80%, 90% or 100% of the antigen or the antigen and one or more other vaccine components of a non-depot-forming vaccine have been cleared from the site of injection with about 3 hours, 6 hours, 12 hours, 18 hours, 24 hours, 36 hours, or 48 hours.

In an embodiment, the methods disclosed herein comprise administering the low dose volume of the composition to a human subject before or after, or both before and after, exposure of the human subject to a virus, bacterium, protozoan or toxin. In an embodiment in which the composition may be used as a preventative vaccine, the methods comprise administering at least one low dose volume of the composition to a human subject before exposure of the human subject to a virus, bacterium, protozoan or toxin.

The human subject may be of any gender and of any age. In an embodiment, the human subject is an infant, a toddler, an adolescent, an adult or an elderly subject. In some embodiments, the human subject is 0-2 years, 50-64 years or over 65 years of age.

The compositions which can be used in the methods disclosed herein are described below. In an embodiment, the composition is a water-free or substantially water-free oil-based composition.

Compositions

As used herein, the terms "vaccine", "vaccine composition" or "composition" may be used interchangeably, as the context requires.

Compositions for use in the methods disclosed herein comprise an antigen comprising a B-cell epitope, an amphipathic compound and a hydrophobic carrier. Each of these components is individually described herein in greater detail, as well as exemplary additional components that may be included in the composition, without limitation. These compositions, to distinguish from other compositions, are referred to herein at various instances (e.g. in the Examples) as "oil-based" compositions.

In an embodiment, the composition is water-free or substantially free of water as described herein.

The compositions are for use in the methods disclosed herein at a low dose volume. In this context, the term "therapeutically effective amount" refers to the quantity (e.g. microgram amount) of the individual components in the low dose volume of the composition. The expression "therapeutically effective amount" is not in reference to the dose volume. As used herein, a "therapeutically effective amount" means an amount of the active ingredient (e.g. antigen) effective to stimulate, induce, maintain, boost or enhance an antibody immune response in a subject. In some embodiments, a therapeutically effective amount of the vaccine is an amount capable of inducing a clinical response in a subject in the treatment of a particular disease or disorder. Determination of a therapeutically effective amount is within the capability of those skilled in the art, especially in light of the disclosure provided herein. The therapeutically effective amount may vary according to a variety of factors such as the subject's condition, weight, sex and age.

i) Antigens

The compositions disclosed herein comprise one or more antigens. At least one of the antigens comprises at least one B-cell epitope. Other antigens, which may or may not include a B-cell epitope, may be included in the compositions.

At least one antigen of the composition comprises a B-cell epitope. Depending on the length of the antigen it may comprise more than one B-cell epitope. For example and without limitation, the antigen may comprise one, two, three, four or five B-cell epitopes.

The B-cell epitope or epitopes may be of any chemical nature, including without limitation peptides, carbohydrates, lipids, glycopeptides and glycolipids. In particular embodiments, the epitopes are peptides derived from one or more of the antigens described herein or known in the art. The epitope may be identical to a naturally occurring epitope, or may be a modified form of a naturally occurring epitope.

B-cell epitopes are recognized by B-cells and by antibodies. B-cell peptide epitopes are typically at least five amino acids, more often at least six amino acids, still more often at least seven or eight amino acids in length, and may be continuous ("linear") or discontinuous ("conformational"); the latter being formed, for example, by the folding of a protein to bring non-contiguous parts of the primary amino acid sequence into physical proximity. Conformational epitopes may be recognizable as linear epitopes, such as when they are synthetically prepared as such. Typically, linear B-cell epitopes vary from 5-20 amino acids in length. B-cell epitopes may also be carbohydrate epitopes.

Experimental methods to identify B-cell epitopes are known in the art. Generally, there are two important aspects to consider when identifying B-cell epitopes. First is the primary amino acid sequence of the protein. Second is the conformational structure of the protein.

The antigen of the compositions described herein may either consist of or comprise a B-cell epitope capable of inducing a humoral immune response.

In some embodiments, the antigen of the compositions described herein may consist of or comprise one or more B-cell epitopes associated with an infectious disease. For example, the antigen may consist of or comprise a B-cell epitope derived from a virus, such as for example influenza virus, Zika virus or respiratory syncytial virus. In an embodiment, the B-cell epitope may be an epitope derived from the hemagglutinin glycoprotein of the H5N1 influenza virus. In another embodiment, the B-cell epitope may be an epitope derived from the ectodomain of the small hydrophobic protein (SHe) of a respiratory syncytial virus.

In another embodiment, the antigen of the compositions described herein may consist of or comprise a B-cell epitope derived from a bacterium, such as for example *Bordetella pertussis* or *Bacillus anthracis*. In an embodiment, the B-cell epitope may be an epitope of the pertussis toxoid protein produced by *Bordetella pertussis*. In another embodiment, the B-cell epitope may be an epitope of the anthrax recombinant protective antigen (rPA) or the anthrax mutant recombinant protective antigen (mrPA).

In another embodiment, the antigen of the compositions described herein may consist of or comprise a B-cell epitope derived from a protozoan, such as from the genus *Plasmodium.*

In a further embodiment, the composition may comprise a mixture of B-cell epitopes as antigens for inducing a humoral immune response. The B-cell epitopes may be linked to form a single molecule (e.g. one polypeptide) or be presented as separate molecules (e.g. separate polypeptides).

In addition to an antigen comprising a B-cell epitope, in some embodiments the compositions described herein may include an antigen that comprises a CTL epitope. In an embodiment, the sequence of the CTL epitope may completely or partially overlap the sequence of the B-cell epitope.

CTL epitopes are molecules recognized by cytotoxic T lymphocytes. CTL epitopes are typically presented on the surface of an antigen-presenting cell, complexed with MHC molecules. As used herein, the term "CTL epitope" refers to a molecule (e.g. peptide) which is substantially the same as a natural CTL epitope of an antigen (including a hapten). The CTL epitope may be modified as compared to its natural counterpart, such as by one or two amino acids. Unless otherwise stated, reference herein to a CTL epitope is to an unbound molecule that is capable of being taken up by cells and presented on the surface of an antigen-presenting cell.

The CTL epitope should typically be one that is amenable to recognition by T cell receptors so that a cell-mediated immune response can occur. For peptides, CTL epitopes may interact with class I or class II MHC molecules. CTL epitopes presented by MHC class I molecules are typically peptides between 8 and 15 amino acids in length, and more often between 9 and 11 amino acids in length. CTL epitopes presented by MHC class II molecules are typically peptides between 5 and 24 amino acids in length, and more often between 13 and 17 amino acids in length. If the antigen is larger than these sizes, it will be processed by the immune system into fragments of a size more suitable for interaction with MHC class I or II molecules. Therefore, CTL epitopes may be part of larger peptides than those mentioned above.

Many CTL epitopes are known. Several techniques of identifying additional CTL epitopes are recognized by the art. In general, these involve preparing a molecule which potentially provides a CTL epitope and characterizing the immune response to that molecule.

In an embodiment, an antigen of the compositions described herein may consist of or comprise a CTL epitope. For example, the antigen may consist of or comprise a CTL epitope derived from a virus, such as HPV or influenza. In another embodiment, the CTL epitope may be an epitope of a tumor-associated protein, such as for example, one or more of the survivin peptides described herein or a melanoma-associated protein. In a further embodiment, the composition may comprise a mixture of CTL epitopes. The CTL epitopes may be linked to form a single molecule (e.g. one polypeptide) or be presented as separate molecules (e.g. separate polypeptides).

In some embodiments, the B-cell and CTL epitopes are disease-associated and/or disease-specific epitopes. Such diseases include, but are not limited to, any of those described herein. For example, and without limitation, the disease may be an infectious disease (such as, for example, a disease caused by or associated with human papillomavirus (HPV) infection, respiratory syncytial virus (RSV) infection, influenza virus infection, Zika virus infection, Ebola virus infection, *Bacillus anthracis* infection, or *Plasmodium malariae* infection); cancer (such as, for example, breast cancer, ovarian cancer, prostate cancer, glioblastoma or diffuse large B cell lymphoma); or an addiction disease (such as, for example, addiction to cocaine).

The compositions described herein comprise at least one antigen comprising at least one B-cell epitope, and may further comprise additional epitopes (B-cell or CTL) on the same or different antigen, which may be linked to form a single molecule (e.g. one polypeptide) or be presented as separate molecules (e.g. separate polypeptides). Exemplary antigens comprising such epitopes are described below, without limitation.

As used herein, the term "antigen" refers to any substance or molecule that can bind specifically to components of the immune system. At least one antigen of the compositions herein comprises a B-cell epitope and is capable of inducing an antibody immune response in a human subject. An antigen that is capable of inducing an immune response is said to be immunogenic, and may also be called an immunogen. Thus, as used herein, the term "antigen" includes immunogens and the terms may be used interchangeably unless specifically stated otherwise. The term antigen, as used herein, also includes haptens. As is understood in the art, a hapten is a small molecule that is antigenic (e.g. capable of being bound by components of the immune system), but is not immunogenic unless it is attached to a carrier molecule of some sort which supplies the immunogenicity.

Antigens that may be useful in the compositions disclosed herein include, for example and without limitation, a polypeptide, a carbohydrate, a microorganism or a part thereof, such as a live, attenuated, inactivated or killed bacterium, virus or protozoan, or part thereof. The antigen may be, for example, a pathogenic biological agent, a toxin, an allergen, a peptide, a suitable native, non-native, recombinant or denatured protein or polypeptide, or a fragment thereof, or an epitope that is capable of inducing or potentiating an immune response in a subject. In some embodiments, the antigen may be one that is derived from an animal (an animal antigen), such as for example a human (a human antigen), or an antigen that is substantially related thereto.

As used herein, the term "derived from" encompasses, without limitation: an antigen that is isolated or obtained directly from an originating source (e.g. a subject); a synthetic or recombinantly generated antigen that is identical or substantially related to an antigen from an originating source; or an antigen which is made from an antigen of an originating source or a fragment thereof. The term "substantially related", in this context, means that the antigen may have been modified by chemical, physical or other means (e.g. sequence modification), but that the resultant product remains capable of generating an immune response to the original antigen or to the disease or disorder associated with the original antigen.

As used herein, the term "antigen" also includes a polynucleotide that encodes a polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present disclosure, the term "antigen", where the context dictates, encompasses such polynucleotides that encode the polypeptide which functions as the antigen.

In some embodiments, the antigen may be one that is associated with an infectious disease, cancer, or an addiction disease.

Viruses, or parts thereof, that may be useful as antigens in the compositions herein include for example, and without limitation, respiratory syncytial virus, human respiratory syncytial virus, influenza virus (e.g. H5N1 influenza virus, influenza A virus, influenza B virus, influenza C virus), Zika virus, human papillomavirus (HPV), Cowpoxvirus, Vaccinia virus, Pseudocowpox virus, herpes virus, Human herpesvirus 1, Human herpesvirus 2, Cytomegalovirus, Human adenovirus A-F, Polyomavirus, Parvovirus, Hepatitis A virus, Hepatitis B virus, Hepatitis C virus, human immunodeficiency virus (HIV), Orthoreovirus, Rotavirus, Ebola virus, parainfluenza virus, Measles virus, Mumps virus, Rubella virus, Pneumovirus, Rabies virus, California encephalitis virus, Japanese encephalitis virus, Hantaanvirus, Lymphocytic choriomeningitis virus, Coronavirus, Enterovirus, Rhinovirus, Poliovirus, Norovirus, Flavivirus, Dengue virus, West Nile virus, Yellow fever virus and varicella.

In an embodiment, the composition disclosed herein comprises an antigen derived from a respiratory syncytial virus (RSV).

RSV is the most common viral cause of acute lower respiratory tract infection in young children worldwide (Nair et al., 2010), and almost all children are infected by the age of two years. Re-infection occurs throughout the lifespan, with significant associated morbidity in older adults (Walsh and Falsey, 2004) and the severely immunocompromised (Khanna et al., 2008). In Canada, RSV-associated lower respiratory tract illness (LRTI) in young children accounts for over 12,000 hospitalizations annually in up to 2% of the birth cohort (Langley et al., 2003). Despite decades of research no intervention has been shown to definitively alter the natural history of established RSV infection, and thus care is generally supportive. Enormous progress in understanding RSV epidemiology, virology, pathogenesis of disease and immune responses in humans has been made, but no safe and effective RSV vaccine is yet available. An RSV vaccine has been identified as a high global priority (Nair et al., 2011), and multiple experimental approaches to overcome the obstacles to vaccine development have been suggested.

Development of RSV vaccines began soon after identification of the virus in 1957 (Chanock and Finberg, 1957; Chanock, Roizman and Myers, 1957). A formalin-inactivated RSV vaccine, designated lot 100, was given by intramuscular injection to preschool children and infants to prevent medically attended infection in the winter of 1966-1967. Infant recipients of the RSV vaccine had a higher frequency of RSV-associated hospitalization than controls and two infants died of RSV infection. Intensive study of these children, replication of the experiment in rodent models, and in vitro studies have led to the hypothesis that the formalin-inactivated vaccine produced inadequate levels of serum neutralizing antibody, low-avidity antibody, no cellular immune response or local immunity, altered immune responses to formalin-modified proteins (Moghaddam, 2006), and induction of a Th2 immune response (Karron, 2013). This phenomenon of vaccine-associated disease enhancement greatly altered the landscape for RSV vaccine development for decades.

RSV vaccine candidates to date have included nasally administered live attenuated biologically derived, genetically engineered, and subunit vaccines, as well as injectable subunit vaccines. Many vaccines are focused on stimulating the host to produce neutralizing antibodies to RSV coat proteins F and G. Advances in molecular biology have led to identification of specific RSV antigenic components, or epitopes (Anderson et al., 2010), to which the human immune response could be directed. As there is no approved vaccine on the market, there is an unmet need for the development and availability of a safe, efficient and cost effective RSV vaccine.

The RSV virion, a member of the genus Paramyxoviridae, is composed of a single strand of negative-sense RNA with 15,222 nucleotides. The nucleotides encode three transmembrane surface proteins (F, G and small hydrophobic protein or SH), two matrix proteins (M and M2), three nucleocapsid proteins (N, P and L), and two non-structural proteins (NS1 and NS2). Subunit vaccines tested in humans to date include a purified F-glycoprotein vaccine, a combined F, G and M protein vaccine developed by Sanofi Pasteur; a conjugated G glycoprotein peptide (BBG2Na) vaccine, and a chimeric RSV FG fusion protein vaccine.

In an embodiment, a composition disclosed herein may include an antigen to any one or more of the RSV proteins. In a particular embodiment, the composition comprises an antigen of the SH protein of RSV or a fragment thereof. In other embodiments, the composition may comprise an antigen of the SH protein of another paramyxovirus of a fragment thereof.

The SH protein, present in a number of paramyxoviruses (Collins et al., 1990), is a transmembrane protein with an ectodomain or "extracellular" component. The human RSV SH protein contains 64 amino acids (Subgroup A) and 65 amino acids (Subgroup B) and is highly conserved.

```
Human RSV SH (Subgroup A):
                                            (SEQ ID NO: 4)
MENTSITIEFSSKFWPYFTLIHMITTIISLLIIISIMIAILNKLCEYNV

FHNKTFELPRARVNT

Human RSV SH (Subgroup B):
                                            (SEQ ID NO: 5)
MGNTSITIEFTSKFWPYFTLIHMILTLISLLIIITIMIAILNKLSEHKT

FCNKTLEQGQMYQINT
```

Although the function of SH was unclear for many years, recent evidence suggests SH appears to function as a viroporin, and signals inflammasome activation and induces membrane permeability to ions or small molecules during RSV infection. The use of SH antigen as a potential vaccine candidate has been explored in preclinical studies by investigators based at the University of Ghent in Belgium, the independent research institute Vlaams Instituutvoor Biotechnologie (VIB; Flanders, Belgium), and Baylor College of Medicine, (Houston Tex.). The VIB group has specifically examined the 23 amino acid ectodomain portion of the SH protein, known as SHe (see e.g. WO 2012/065997). However, SHe is a small peptide so the immunogenicity of SHe alone is limited.

In an embodiment, the composition disclosed herein includes an antigen that comprises or consists of the ectodomain of the SH protein (SHe) of a paramyxovirus, or a fragment thereof. In an embodiment, SHe is derived from bovine RSV. In other embodiments, SHe is derived from a subgroup A human RSV strain or a subgroup B human RSV strain.

```
Subgroup A human RSV SHe (RSV SHe A):
                                            (SEQ ID NO: 1)
NKLCEYNVFHNKTFELPRARVNT Subgroup B human RSV SHe (RSV SHe B):
                                            (SEQ ID NO: 2)
NKLSEHKTFCNKTLEQGOMYQINT
```

Therefore, in some embodiments, the composition disclosed herein includes an antigen comprising or consisting of the amino acid sequence NKLCEYNVFHNKTFELPRARVNT (SEQ ID NO: 1) or a fragment thereof. In some embodiments, the composition disclosed herein includes an antigen comprising or consisting of the amino acid sequence NKLSEHKTFCNKTLEQGQMYQINT (SEQ ID NO: 2) or a fragment thereof.

In some embodiments, the composition comprises an antigen that consists of the amino acid sequence NKLCEYNVFHNKTFELPRARVNT (SEQ ID NO: 1).

In some embodiments, the composition comprises an antigen that consists of the amino acid sequence NKLSEHKTFCNKTLEQGQMYQINT (SEQ ID NO: 2).

In some embodiments, the amino acid sequence of the SHe may be modified by insertions, deletions and/or amino acid substitutions. In these and other embodiments, the SHe may comprise an amino acid sequence that is at least 50%, at least 55%, at least 60%, at least 65%, at least 70%, at least 75%, at least 80%, at least 85%, at least 90% or at least 95% identical to the SHe of SEQ ID NO: 1 or 2. Sequence alignments can be measured, for example, in a BLASTp alignment (Altschul et al., 1997). Exemplary embodiments of variants of the SHe sequence are disclosed, for example, in WO 2012/065997 (see e.g. the sequences of SEQ ID NOs: 3-30 in WO 2012/065997).

In some embodiments, an antigen comprising an SHe may comprise or consist of the amino acid sequence NKLSEYNVFHNKTFELPRARVNT (SEQ ID NO: 6). In some embodiments, the composition comprises an antigen that consists of the sequence NKLSEYNVFHNKTFELPRARVNT (SEQ ID NO: 6).

When the compositions disclosed herein comprise an antigen comprising SHe or a fragment or variant thereof, it may be present in the compositions in monomeric form, dimeric form, or another oligomeric form, or any combination thereof. In an embodiment, an antigen comprising SHe A and/or SHe B is a monomer (e.g. a single polypeptide). In another embodiment, an antigen comprising SHe A and/or SHe B is dimer (e.g. two separate polypeptides dimerized). Means of dimerization are known in the art. An exemplary procedure is to dissolve the RSV SHe peptide antigens in a mixture of 10% DMSO/0.5% acetic acid in water (w/w) and heat at 37° C. overnight.

In an embodiment, the composition disclosed herein comprises an antigen comprising RSV SHe A or a fragment or variant thereof as a monomer.

In an embodiment, the composition disclosed herein comprises an antigen comprising RSV SHe A or a fragment or variant thereof as a dimer.

In an embodiment, the composition disclosed herein comprises an antigen comprising RSV SHe B or a fragment or variant thereof as a monomer.

In an embodiment, the composition disclosed herein comprises an antigen comprising RSV SHe B or a fragment or variant thereof as a dimer.

As described for example in WO 2012/065997, the SHe peptide antigen may be genetically or chemically linked to a carrier. Exemplary embodiments of carriers suitable for presentation of peptide antigens are known in the art, some of which are described in WO 2012/065997. In another embodiment, the SHe peptide antigen may be linked to an amphipathic compound as described herein or a structure formed therefrom.

In another embodiment, a composition disclosed herein comprises an antigen derived from an influenza virus. Influenza is a single-stranded RNA virus of the family Orthomyxoviridae and is often characterized based on two large glycoproteins on the outside of the viral particle, hemagglutinin (HA) and neuraminidase (NA). Numerous HA subtypes of influenza A have been identified (Kawaoka et al. 1990; Webster et al. 1983). In some embodiments, the antigen may be derived from the HA or NA glycoproteins. In a particular embodiment, the antigen may be recombinant HA antigen (H5N1, A/Vietnam/1203/2004; Protein Sciences; USA), such as derived from the sequence found under Genbank Accession number AY818135 or any suitable sequence variant thereof.

In another embodiment, a composition disclosed herein comprises an antigen derived from Ebola virus.

In another embodiment, a composition disclosed herein comprises an antigen derived from human papillomavirus (HPV). In more particular embodiments, a composition disclosed herein comprises an antigen associated with HPV-related cervical cancer or HPV-related head and neck cancer. In some embodiments, the antigen is a peptide comprising the sequence RAHYNIVTF (HPV16E7 (H-2db) peptide 49-57; R9F; SEQ ID NO: 7).

Bacteria or parts thereof that may be useful as antigens in the compositions herein include for example, and without limitation, Anthrax (*Bacillus anthracis*), *Brucella*, *Bordetella pertussis*, *Candida*, *Chlamydia pneumoniae*, *Chlamydia psittaci*, Cholera, *Clostridium botulinum*, Coccidioidesimmitis, *Cryptococcus*, Diphtheria, *Escherichia coli* O157: H7, Enterohemorrhagic *Escherichia coli*, Enterotoxigenic *Escherichia coli*, *Haemophilus influenzae*, *Helicobacter pylori*, *Legionella*, *Leptospira*, *Listeria*, Meningococcus, *Mycoplasma pneumoniae*, *Mycobacterium*, Pertussis, Pneumonia, *Salmonella*, *Shigella*, *Staphylococcus*, *Streptococcus pneumoniae* and *Yersinia enterocolitica*.

In an embodiment, a composition disclosed herein comprises an antigen derived from a *Bacillus anthracis*. Without limitation, the antigen contained in the composition may for example be derived from anthrax recombinant protective antigen (rPA) (List Biological Laboratories, Inc.; Campbell, Calif.) or anthrax mutant recombinant protective antigen (mrPA) (Pfenex, Inc.; San Diego, Calif.). In some embodiments the antigen may be derived from the sequence found under Genbank Accession number P13423, or any suitable sequence variant thereof.

Protozoa or parts thereof that may be useful as antigens in the compositions herein include for example, and without limitation, the genus *Plasmodium* (*Plasmodium falciparum*, *Plasmodium malariae*, *Plasmodium vivax*, *Plasmodium ovale* or *Plasmodium knowlesi*), which causes malaria.

In an embodiment, a composition disclosed herein comprises an antigen derived from a *Plasmodium malariae*.

The antigen may alternatively be a naturally occurring or synthesized toxin or allergen. A "toxin", as used herein, refers to any substance produced by living cells or organisms (e.g. plants, animals, microorganisms, etc.) that is capable of causing a disease or ailment, or an infectious substance, or a recombinant or synthesized molecule capable of adverse effect. Toxins may be for example small molecules, peptides, or proteins. Toxins include drug substances such as, for example, cocaine. The toxin may be capable of being neutralized by an antibody. In such embodiments, the antigen may elicit the production of antibodies that bind to and sequester the toxin in circulation (e.g. the blood), thereby potentially preventing its delivery to another area of the body (e.g. the brain).

An "allergen", as used herein, refers to any substance that can cause an allergy. The allergen may be derived from, without limitation, cells, cell extracts, proteins, polypeptides, peptides, polysaccharides, polysaccharide conjugates, peptide and non-peptide mimics of polysaccharides and other molecules, small molecules, lipids, glycolipids, and carbohydrates of plants, animals, fungi, insects, food, drugs, dust, and mites. Allergens include but are not limited to environmental aeroallergens; plant pollens (e.g. ragweed/hayfever); weed pollen allergens; grass pollen allergens; Johnson grass; tree pollen allergens; ryegrass; arachnid allergens (e.g. house dust mite allergens); storage mite allergens; Japanese cedar pollen/hay fever; mold/fungal spore allergens; animal allergens (e.g. dog, guinea pig, hamster, gerbil, rat, mouse, etc., allergens); food allergens (e.g. crustaceans; nuts; citrus fruits; flour; coffee); insect allergens (e.g. fleas, cockroach); venoms: (Hymenoptera, yellow jacket, honey bee, wasp, hornet, fire ant); bacterial allergens (e.g. streptococcal antigens; parasite allergens such as *Ascaris* antigen); viral antigens; drug allergens (e.g. penicillin); hormones (e.g. insulin); enzymes (e.g. streptokinase); and drugs or chemicals capable of acting as incomplete antigens or haptens (e.g. the acid anhydrides and the isocyanates).

Where a hapten is used in a composition disclosed herein, it may be attached to a carrier or another antigen described herein, such as for example a protein, to form a hapten-carrier adduct. The hapten-carrier adduct is capable of eliciting an immune response, whereas the hapten itself would not typically elicit a response. Non-limiting examples of haptens are aniline, urushiol (a toxin in poison ivy), hydralazine, fluorescein, biotin, digoxigenin and dinitrophenol.

In another embodiment, the antigen may be an antigen associated with a disease where it is desirable to sequester the antigen in circulation, such as for example an amyloid protein (e.g. Alzheimer's disease). Thus, in some embodiments, a composition as disclosed herein comprises an antigen that may potentially be useful in the treatment and/or prevention of a neurodegenerative disease in a subject in need thereof, wherein the neurodegenerative disease is associated with the expression of the antigen.

In another embodiment, the antigen may be derived from a cancer or tumor-associated protein, such as for example, a membrane surface-bound cancer antigen which is capable of being recognized by an antibody.

In an embodiment, the cancer may be one that is caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. Thus, in an embodiment, a composition disclosed herein may comprise an antigen derived from a virus that is linked to the development of cancer. Exemplary cancers that may benefit from the methods and compositions disclosed herein include any malignant cell that expresses one or more tumor specific antigens, and for example cancers expressing a membrane surface-bound cancer antigen which is capable of being recognized by an antibody.

Many cancer or tumor-associated proteins are known in the art such as for example, and without limitation, those described in WO 2007/041832 and International Application PCT/CA2016/050487. For example, the cancer-associated antigen may be derived from HPV (e.g. E6, E7, L1 or L2 protein; or one or more of the HPV antigens disclosed in WO1993/022338, WO2002/070006, WO2006/115413, WO2008/147187, WO2009/002159 or WO2010/123365) or the membrane surface-bound protein survivin (see e.g. WO2014/153636, WO 2004/067023 and WO 2006/081826), or a variant or fragment thereof. These antigens may be included in the compositions disclosed herein if they comprise a B-cell epitope or if they are used as an additional antigen in the composition.

In some embodiments, the compositions comprise antigens that are weakly immunogenic. As used herein, by "weakly immunogenic" it is meant that in conventional vaccines (e.g. aqueous vaccines, emulsions, etc.), the antigens have little or no ability to induce, maintain and/or boost an immune response.

For example, in an embodiment, a weakly immunogenic antigen is one that when formulated in an aqueous vaccine, is unable to sufficiently induce an immune response. This is in contrast to when the same antigen is formulated in a comparable vaccine composition as disclosed herein (i.e. having the same components, except formulated in a hydrophobic carrier with an amphipathic compound), whereby the antigen is now able to sufficiently induce an immune response. In the preceding context, "sufficiently induce an immune response" means that the antigen is able to induce an antibody immune response in a human subject to the extent that it results in detectable antibody titers as described in the examples herein (i.e. at the limit of detection of 1/100 dilution).

In an embodiment, a weakly immunogenic antigen is one that upon exposure to the subject in an aqueous vaccine, induces no immune response or induces an immune response that is at least 2 times, 3 times, 4 times, 5 times, 6 times, 7 times, 8 times, 9 times, 10 times or more less efficacious as compared to the immune response induced upon exposure to the subject in a composition as described herein.

In an embodiment, a weakly immunogenic antigen is one that when administered in an aqueous vaccine is unable to provide a measurable therapeutic benefit to the subject; whereas a measurable therapeutic benefit can be achieved when the antigen is administered in a composition as disclosed herein. In an embodiment, the measureable therapeutic benefit may, for example, be an antibody immune response with detectable antibody titer at the limit of detection (1/100 dilution) as described herein.

Without limitation, weakly immunogenic antigens may include, for example, purified and synthetic peptide antigens; self-antigens; cancer-associated antigens; or neoantigens.

In an embodiment, a composition disclosed herein comprises an antigen that is a self-antigen. As is well-known in the art, a self-antigen is an antigen that originates from within the body of a subject. The immune system is usually non-reactive against self-antigens under normal homeostatic conditions. These types of antigens therefore pose a difficulty in the development of targeted immune therapies.

In an embodiment, a composition disclosed herein comprises a neoantigen. Neoantigens which may be included in the compositions are, for example and without limitation, those described in U.S. Provisional Application No. 62/331,770 filed on May 4, 2016.

In an embodiment, the antigen contained in the compositions may comprise a mixture of one or more of the antigens described herein, optionally fused together as a fused protein with or without spacer sequences between the antigens.

In an embodiment, the antigen is a polypeptide derived from any of the antigens described herein. In an embodiment, the antigen is a peptide antigen of 5 to 50 amino acids in length.

For example, and without limitation, polypeptides or fragments thereof that may be useful as antigens in the compositions herein include those derived from the ectodomain of the small hydrophobic (SH) protein of RSV, Cholera toxoid, tetanus toxoid, diphtheria toxoid, hepatitis B surface antigen, hemagglutinin (e.g. H5N1 recombinant hemagglutinin protein), anthrax recombinant protective antigen (List Biological Laboratories, Inc.; Campbell, Calif.), anthrax mutant recombinant protective antigen (Pfenex, Inc.; San Diego, Calif.), neuraminidase, influenza M protein, PfHRP2, pLDH, aldolase, MSP1, MSP2, AMA1, Der-p-1, Der-f-1, Adipophilin, AFP, AIM-2, ART-4, BAGE, α-feto protein, BCL-2, Bcr-Abl, BING-4, CEA, CPSF, CT, cyclin D1Ep-CAM, EphA2, EphA3, ELF-2, FGF-5, G250, Gonadotropin Releasing Hormone (GNRH), HER-2, intestinal carboxyl esterase (iCE), IL13Rα2, MAGE-1, MAGE-2, MAGE-3, MART-1, MART-2, M-CSF, MDM-2, MMP-2, MUC-1, NY-EOS-1, MUM-1, MUM-2, MUM-3, pertussis toxoid protein, p53, PBF, PRAME, PSA, PSMA, RAGE-1, RNF43, RU1, RU2AS, SART-1, SART-2, SART-3, SAGE- 1, SCRN 1, SOX2, SOX10, STEAP1, survivin, Telomerase, TGFβRII, TRAG-3, TRP-1, TRP-2, TERT and WT1.

The term "polypeptide" encompasses any chain of amino acids, regardless of length (e.g. at least 6, 8, 10, 12, 14, 16, 18, or 20 amino acids) or post-translational modification (e.g. glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitution |
| --- | --- |
| Ala | Ser |
| Arg | Lys |
| Asn | Gln, His |
| Asp | Glu |
| Cys | Ser |
| Gln | Asn |
| Glu | Asp |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Val | Ile, Leu |

Polypeptides or peptides that have substantial identity to an antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.jp, the local homology algorithm of Smith and Waterman (1981), the homology alignment algorithm of Needleman and Wunsch (1970), the search for similarity method of Pearson and Lipman (1988), and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990) (using the published default settings). For example, the "BLAST 2 Sequences" tool, available through the National Center for Biotechnology Information (through the internet at http://www.ncbi.nlm.nih.gov/BLAST/bl2seq/wblast2.cgi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g. Caruthers 1980, Horn 1980, Banga, 1995. For example, peptide synthesis can be performed using various solid-phase techniques (see e.g. Roberge 1995, Merrifield 1997) and automated synthesis may be achieved, e.g. using the ABI 431A Peptide Synthesizer (Perkin Elmer) in accordance with the instructions provided by the manufacturer.

In some embodiments, the antigen may be a purified antigen, e.g. from about 25% to about 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the term "antigen" also includes a polynucleotide that encodes the polypeptide that functions as an antigen. As used herein, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition as disclosed herein is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

The amount (quantity) of antigen used in a single low dose volume administration of a composition as described herein may vary depending on the type of antigen and characteristics of the subject (e.g. size, weight, age, sex, etc.). One skilled in the art will be able to determine, without undue experimentation, the effective amount of antigen to use in a particular application. The term "effective amount" as used herein means an amount effective, for periods of time necessary, to achieve the desired result.

In an embodiment, the composition may comprise between about 5-50 micrograms of the antigen per low dose volume administration to a human subject. In some embodiments thereof, the composition comprises about 5 µg, about 10 µg, about 15 µg, about 20 µg, about 25 µg, about 30 µg, about 35 µg, about 40 µg, about 45 µg, or about 50 µg of the antigen per low dose volume administration to a human subject. In an embodiment, the composition comprises about 10 µg of the antigen per low dose volume administration to a human subject. In another embodiment, the composition comprises about 25 µg of the antigen per low dose volume administration to a human subject.

In some embodiments the antigen is itself sufficiently hydrophobic such that the antigen is miscible in the hydrophobic carrier. In some embodiments, the antigen is made sufficiently hydrophobic (e.g. by the amphipathic compound) such that the antigen is miscible in the hydrophobic carrier.

ii) Amphipathic Compound

An "amphipathic compound" is a compound having both hydrophilic and hydrophobic (lipophilic) parts or characteristics. The term "amphipathic compound" may be used interchangeably with "amphiphile" or "amphiphilic". In some embodiments, suitable amphipathic compounds may also include emulsifiers such as those described herein below. Exemplary embodiments of emulsifiers that are encompassed herein by the term "amphipathic compound" include, without limitation, polysorbates (e.g. sorbitan monooleate), mannide oleate (Arlacel™ A), lecithin, Tween™ 80, and Spans™ 20, 80, 83 and 85. The amphipathic compound can facilitate the incorporation of vaccine components with hydrophilic affinity into a hydrophobic carrier such as an oil in the absence of water. The vaccine components can include, without limitation, antigens and/or adjuvants and/or other ingredients that can facilitate the production of an immune response.

Without limitation, the hydrophobic portion of an amphipathic compound is typically a large hydrocarbon moiety, such as a long chain of the form $CH_3(CH_2)_n$, with $n>4$. The hydrophilic portion of an amphipathic compound is usually either a charged group or a polar uncharged group. Charged groups include anionic and cationic groups. Examples of anionic charged groups include the following (wherein the hydrophobic part of the molecule is represented by "R"): carboxylates: $RCO_2^-$; sulfates: $RSO_4^-$; sulfonates: $RSO_3^-$; and phosphates (the charged functionality in phospholipids). Cationic charged groups include e.g. amines: $RNH_3^+$ ("R" again representing the hydrophobic part of the molecule). Uncharged polar groups include e.g. alcohols with large R groups, such as diacyl glycerol (DAG). Amphipathic compounds may have several hydrophobic parts, several hydrophilic parts, or several of both. Proteins and some block copolymers are examples. Steroids, cholesterol, fatty acids, bile acids, and saponins, are also amphiphiles.

There are numerous amphipathic compounds which may be used, and the vaccine compositions disclosed herein may contain a single type of amphipathic compound or a mixture of different types of amphipathic compounds.

In an embodiment, the amphipathic compound is a lipid or a lipid mixture. Although any amphiphilic lipid may be used, particularly suitable lipids may include those with at least one fatty acid chain containing at least 4 carbons, and typically about 4 to 28 carbons in length. The fatty acid chain may contain any number of saturated and/or unsaturated bonds. The lipid may be a natural lipid or a synthetic lipid. Non-limiting examples of amphiphilic lipids may include phospholipids, sphingolipids, sphingomyelin, cerobrocides, gangliosides, ether lipids, sterols, cardiolipin, cationic lipids and lipids modified with poly (ethylene glycol) and other polymers. Synthetic lipids may include, without limitation, the following fatty acid constituents: lauroyl, myristoyl, palmitoyl, stearoyl, arachidoyl, oleoyl, linoleoyl, erucoyl, or combinations of these fatty acids.

In an embodiment, the amphipathic compound is a phospholipid or a mixture of phospholipids. Broadly defined, a "phospholipid" is a member of a group of lipid compounds that yield on hydrolysis phosphoric acid, an alcohol, fatty acid, and nitrogenous base.

Phospholipids that may be used include for example, and without limitation, those with at least one head group selected from the group consisting of phosphoglycerol, phosphoethanolamine, phosphoserine, phosphocholine (e.g. DOPC; 1,2-Dioleoyl-sn-glycero-3-phosphocholine) and phosphoinositol. In some embodiments, a mixture of DOPC and unesterified cholesterol may be used. In other embodiments, a mixture of Lipoid S100 lecithin and unesterified cholesterol may be used. When unesterified cholesterol is used, the cholesterol may be used in an amount equivalent to about 10% of the weight of phospholipid (e.g. in a DOPC:cholesterol ratio of 10:1 w/w or a S100 lecitin:cholesterol ratio of 10:1 w/w). The cholesterol is used to stabilize the formation of phospholipid vesicles. If a compound other than cholesterol is used, one skilled in the art can readily determine the amount needed.

Another common phospholipid is sphingomyelin. Sphingomyelin contains sphingosine, an amino alcohol with a long unsaturated hydrocarbon chain. A fatty acyl side chain is linked to the amino group of sphingosine by an amide bond, to form ceramide. The hydroxyl group of sphingosine is esterified to phosphocholine. Like phosphoglycerides, sphingomyelin is amphipathic.

Lecithin, which also may be used, is a natural mixture of phospholipids typically derived from chicken eggs or sheep's wool.

All of these and other phospholipids may be used in the practice of the invention. Phospholipids can be purchased, for example, from Avanti lipids (Alabastar, Ala., USA), and lipoid LLC (Newark, N.J., USA).

In an embodiment, the amphipathic compound may be substantially evenly dispersed in the hydrophobic carrier, whereby the presence of the amphipathic compound alone is sufficient to facilitate the incorporation of vaccine components with hydrophilic affinity (e.g. an antigen) into a hydrophobic carrier.

In another embodiment, the amphipathic compound may be closely associated with the antigen so as to make the antigen miscible in the hydrophobic carrier. By "closely associated", it is meant that the amphipathic compound is in such proximity with the antigen that the antigen is presented in a form that it is miscible in the hydrophobic carrier. The close association may or may not involve physical interaction between the antigen and the amphiphile. Typically, the hydrophilic part of the amphipathic compound is oriented towards the hydrophilic moieties on the antigen. The amphipathic compounds may remain substantially separate from one another or they may form various different types of structures, assemblies or arrays.

Exemplary embodiments of the types of structures, assemblies or arrays that the amphipathic compounds may form include, without limitation: single layer sheets, bilayer sheets, multilayer sheets, single layer vesicular structures (e.g. micelles), bilayer vesicular structures (e.g. unilamellar or multilamellar vesicles), or various combinations thereof. By "single layer" it is meant that the amphipathic compounds do not form a bilayer, but rather remain in a layer with the hydrophobic part oriented on one side and the hydrophilic part oriented on the opposition side. By "bilayer" it is meant that the amphipathic compounds form a two-layered sheet, typically with the hydrophobic part of each layer internally oriented toward the center of the bilayer with the hydrophilic part externally oriented. However, the opposite configuration is also possible. The term "multilayer" is meant to encompass any combination of single and bilayer structures. The form adopted may depend upon the specific antigen, the specific amphipathic compound, and/or the specific hydrophobic carrier that is used.

In an embodiment, the structure, assembly or array formed by the amphipathic compound may partially or completely surround the antigen. As an example, the amphipathic compound may form a closed vesicular structure around the antigen. As another example, preformed structures (e.g. presomes) may surround the antigen and/or engulf the antigen by disassembly/reassembly.

In an embodiment, the vesicular structure is a single layer vesicular structure. An example of such a structure is a micelle. A typical micelle in aqueous solution forms an aggregate with the hydrophilic parts in contact with the surrounding aqueous solution, sequestering the hydrophobic parts in the micelle center. In contrast, in a hydrophobic carrier, an inverse/reverse micelle forms with the hydrophobic parts in contact with the surrounding aqueous solution, sequestering the hydrophilic parts in the micelle center. A spherical reverse micelle can package an antigen with hydrophilic affinity within its core.

In an embodiment, the vesicular structure is a micelle or an inverse/reverse micelle. Without limitation, the size of the micelles or inverse/reverse micelles range from 2 nm (20 A) to 20 nm (200 A) in diameter. In a particular embodiment, the size of the micelles or inverse/reverse micelles is about 10 nm in diameter.

In another embodiment, the vesicular structure is a bilayer vesicular structure, such as for example, a liposome. Liposomes are completely closed lipid bilayer membranes containing an entrapped aqueous volume. Liposomes may be unilamellar vesicles (possessing a single bilayer membrane) or multilamellar vesicles characterized by multimembrane bilayers; each bilayer may or may not be separated from the next by an aqueous layer. A general discussion of liposomes can be found in Gregoriadis 1990 and Frezard 1999. Liposomes can adsorb to virtually any type of cell and then release an incorporated agent (e.g. antigen). Alternatively, the liposome can fuse with the target cell, whereby the contents of the liposome empty into the target cell. Alternatively, a liposome may be endocytosed by cells that are phagocytic.

Liposomes have been used in the preparation of compositions comprising a hydrophobic carrier as a vesicle to encapsulate antigens as well as an emulsifier to stabilize the formulation (see e.g. WO2002/038175, WO2007/041832, WO2009/039628, WO2009/146523 and WO2013/049941). Hydrophilic antigens are typically entrapped in the aqueous interior, while hydrophobic antigens can be intercalated in the lipid bilayer or dispersed in the oil phase. In another embodiment, pre-manufactured liposomes may be used in the vaccine compositions disclosed herein.

In an embodiment, the vesicular structure is a presome. As used herein, "presome" refers to nanoparticles in the size range of ≤110 nm and polydispersity index (pdi) of <0.1. The presomes may comprise, for example, liposomes predominantly with bilayers forming spherical unilamellar liposomes and a mixture of spherical multilamellar liposomes, oblong unilamellar liposomes, oblong multilamellar liposomes and oblong multivesicular liposomes.

Other embodiments of bilayer and mutilayer vesicular structures include, without limitation: niosomes, transfersomes, virosomes, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these vesicular structures are well known in the art (see e.g. Kreuter 1994).

In some embodiments, amphipathic compound may form any combination of the structures described herein within a single formulation of the composition. For example, the composition may comprise multiple different structures, assemblies or arrays. In an embodiment, the composition may comprise structures that resemble liposome bilayers, spherical unilamellar liposomes, spherical multilamellar liposomes, oblong unilamellar liposomes, and oblong multivesicular liposomes.

iii) Hydrophobic Carrier

The compositions disclosed herein comprise a hydrophobic carrier, preferably a liquid hydrophobic substance.

The hydrophobic carrier may be an essentially pure hydrophobic substance or a mixture of hydrophobic substances. Hydrophobic substances that are useful in the compositions described herein are those that are pharmaceutically and/or immunologically acceptable. The carrier is typically a liquid but certain hydrophobic substances that are not liquids at atmospheric temperature may be liquefied, for example by warming, and may also be useful.

Oil or a mixture of oils is a particularly suitable carrier for use in the compositions disclosed herein. Oils should be pharmaceutically and/or immunologically acceptable. Suitable oils include, for example, mineral oils (especially light or low viscosity mineral oil such as Drakeol® 6VR), vegetable oils (e.g. soybean oil), nut oils (e.g. peanut oil), or mixtures thereof. Thus, in an embodiment the hydrophobic carrier is a hydrophobic substance such as vegetable oil, nut oil or mineral oil. Animal fats and artificial hydrophobic polymeric materials, particularly those that are liquid at atmospheric temperature or that can be liquefied relatively easily, may also be used.

In some embodiments, the hydrophobic carrier may be, or comprise, Incomplete Freund's Adjuvant (IFA), a mineral oil-based model hydrophobic carrier. In another embodiment, the hydrophobic carrier may be, or comprise, a mannide oleate in mineral oil solution, such as that commercially available as Montanide® ISA 51 (SEPPIC, France). While these carriers are commonly used to prepare water-in-oil emulsions, the present disclosure avoids this type of formulation by use of an amphipathic compound to suspend the components in the absence of substantial quantities of water, as described herein.

Immunovaccine Inc. has developed vaccine delivery platforms referred to as VacciMax® and DepoVax™ (DPX) (see e.g. U.S. Pat. Nos. 6,793,923 and 7,824,686; WO2002/038175; WO2007/041832; WO2009/039628; WO2009/043165 and WO2009/146523). DPX is a lipid-in-oil formulation that can be formulated with any antigen, or mixture of antigens. Unlike water-in-oil emulsion based vaccines, which rely on oil entrapping water droplets containing antigen and adjuvant, DepoVax™ based formulations rely on lipids to facilitate the incorporation of antigens and adjuvants directly into the oil, without the need for emulsification. Advantages of this approach include: (1) enhancing the solubility of hydrophilic antigens/adjuvant in oil diluents which otherwise would normally have maximum solubility in aqueous-based diluents, and (2) the elimination of cumbersome emulsification procedures prior to vaccine administration.

In some embodiments, the vaccine compositions disclosed herein may comprise Immunovaccine Inc.'s delivery platform DepoVax™.

In an embodiment, the composition comprises: (i) a peptide comprising the amino acid sequence NKLCEYNVFHNKTFELPRARVNT (SEQ ID NO: 1); (ii) a lipid mixture comprising dioleoyl phosphatidylcholine (DOPC) and cholesterol; (iii) a short synthetic lipopeptide which is PAM₃Cys-Ser-(Lys)4 (SEQ ID NO: 3); and (iv) Montanide® ISA 51 VG.

iv) Other Components

The compositions disclosed herein may further comprise one or more additional components as are known in the art (see e.g. Remington's Pharmaceutical Sciences, Mack Publishing Company, Easton, Pa., USA 1985; and The United States Pharmacopoeia: The National Formulary (USP 24 NF19) published in 1999).

In some embodiments, the compositions may additionally comprise an adjuvant, an emulsifier, a T-helper epitope and/or an excipient.

Adjuvants

In some embodiments, the compositions disclosed herein may comprise one or more adjuvants.

A large number of adjuvants have been described and are known to those skilled in the art. Exemplary adjuvants include, without limitation, alum, other compounds of aluminum, *Bacillus* of Calmette and Guerin (BCG), TiterMax™, Ribi™, Freund's Complete Adjuvant (FCA), CpG-containing oligodeoxynucleotides (CpG ODN), lipid A mimics or analogs thereof, lipopeptides and polyI:C polynucleotides.

In some embodiments, the compositions may comprise a lipopeptide as an adjuvant. An exemplary lipopeptide includes, without limitation, PAM₃Cys-SKKK (SEQ ID NO: 3) (EMC Microcollections, Germany) or variants, homologs and analogs thereof. The Pam2 family of lipopeptides (e.g. PAM₂Cys-SKKK; SEQ ID NO: 3) has been shown to be an effective alternative to the Pam3 family of lipopeptides.

In some embodiments, the compositions may comprise a CpG ODN as an adjuvant. An exemplary CpG ODN is 5'-TCCAT<u>GACGTT</u>CCT<u>GACGTT</u>-3' (SEQ ID NO: 8). The skilled person can readily select other appropriate CpG ODNs on the basis of the target species and efficacy.

In some embodiments, the compositions may comprise a polyI:C polynucleotide as an adjuvant.

PolyI:C polynucleotides are polynucleotide molecules (either RNA or DNA or a combination of DNA and RNA) containing inosinic acid residues (I) and cytidylic acid residues (C), and which induce the production of inflammatory cytokines, such as interferon. In some embodiments, the polyI:C polynucleotide is double-stranded. In such embodiments, they are typically composed of one strand consisting entirely of cytosine-containing nucleotides and one strand consisting entirely of inosine-containing nucleotides, although other configurations are possible. For instance, each strand may contain both cytosine-containing and inosine-containing nucleotides. In some instances, either or both strand may additionally contain one or more non-cytosine or non-inosine nucleotides.

In another embodiment, the poly I:C polynucleotide may be a single-stranded molecule containing inosinic acid residues (I) and cytidylic acid residues (C). As an example, and without limitation, the single-stranded poly I:C may be a sequence of repeating dIdC. In a particular embodiment, the sequence of the single-stranded polyI:C may be a 26-mer sequence of $(IC)_{13}$, i.e. ICICICICICICICICICICICIC (SEQ ID NO: 9). As the skilled person will appreciate, due to their nature (e.g. complementarity), it is anticipated that these single-stranded molecules of repeating dIdC would naturally form homodimers, so they are conceptually similar to polyI/polyC dimers.

It has been reported that poly I:C can be segmented every 16 residues without an effect on its interferon activating potential (Bobst 1981). Furthermore, the interferon inducing potential of a poly I:C molecule mismatched by introducing a uridine residue every 12 repeating cytidylic acid residues (Hendrix 1993), suggests that a minimal double stranded poly I:C molecule of 12 residues is sufficient to promote interferon production. Others have also suggested that regions as small as 6-12 residues, which correspond to 0.5-1 helical turn of the double stranded polynucleotide, are capable of triggering the induction process (Greene 1978). If synthetically made, poly I:C polynucleotides are typically about 20 or more residues in length (commonly 22, 24, 26, 28 or 30 residues in length). If semi-synthetically made (e.g. using an enzyme), the length of the strand may be 500, 1000 or more residues.

Poly I:C acts as a mimic of viral genomes and is particularly useful for modulating the immune system in vivo. Synthetic poly I:poly C homopolymers for example have been reported to enhance innate immunity by inducing interferon gamma non-specifically when delivered systemically in vivo by intravenous or intramuscular injection (Krown 1985, Zhu 2007). Several variants of poly inosinic and cytidylic acid polymers have been described over the years (de Clercq 1978, Bobst 1981, de Clercq 1975, Guschlbauer 1977, Fukui 1977, Johnston 1975, U.S. Pat. No. 3,906,092, Kamath 2008, Ichinohe 2007), some of which included the use of covalently modified residues, the use of ribo and deoxy-riboinosinic and cytidylic residues, the use of homopolymers and alternating co-polymers that contain inosinic and cytidylic acid residues, and the introduction of specific residues to create mismatched polymers.

The use of double stranded polynucleotides containing inosinic and cytidylic acids has been reported for the treatment of a number of viral diseases (Kende 1987, Poast 2002, U.S. Pat. No. 6,468,558, Sarma 1969, Stephen 1977, Levy 1978), cancer (Durie 1985, Salazar 1996, Theriault 1986, Nakamura 1982, Talmadge 1985, Droller 1987), autoimmune diseases like multiple sclerosis (Bever 1986), and other infectious diseases such as malaria (Awasthi 1997, Puri 1996). The efficacy of polyI:C molecules has been further enhanced in some cases by complexing the molecule with positively charged poly-lysine and carboxymethylcellulose, effectively protecting the polynucleotide from nuclease degradation in vivo (Stephen 1977, Levy 1985), or by complexing polyI:C with positively charged synthetic peptides (Schellack 2006).

In addition to its use as a non-specific enhancer of innate immunity, polyI:C is also useful as an adjuvant in vaccine compositions. The enhancement of innate immunity can lead to an enhanced antigen specific adaptive immunity, possibly through a mechanism that involves, at least in part, NK cells, macrophages and/or dendritic cells (Chirigos 1985, Salem 2006, Alexopoulou 2001, Trumpfheller 2008). Evidence for the use of polyI:C molecules in this context originates from various vaccine studies for controlling infectious diseases (Houston 1976, Stephen 1977, Ichinohe 2007, Sloat 2008, Agger 2006, Padalko 2004) and the prevention or treatment of cancer by a variety of vaccine modalities (Zhu 2007, Cui 2006, Salem 2005, Fujimura 2006, Llopiz 2008). These studies demonstrate that polyI:C enhances humoral responses as evident from enhanced antibody responses against specific infectious disease antigens. PolyI:C is also a potentiator of antigen-specific cellular responses (Zhu 2007, Zaks 2006, Cui 2006, Riedl 2008). The adjuvanting effects of polyI:C molecules are believed to occur, at least partially, by inducing interferon-gamma through their interaction with toll like receptors (TLR) such as TLR3, TLR4, TLR7, TLR8 and TLR9 (Alexopoulou 2001, Trumpfheller 2008, Schellack 2006, Riedl 2008), with TLR3 being particularly relevant for most polyI:C molecules. Evidence also suggests that polyI:C molecules may exert their effect, at least in part, by interacting with receptors other than TLRs, such as the RNA helicase retinoic acid induced protein I (RIG-I)/melanoma differentiation associated gene 5 (MDA5) (Alexopoulou 2001, Yoneyama 2004, Gowen 2007, Dong 2008). The mechanism of action of polyI:C molecules remains to be fully understood.

Accordingly, as used herein, a "polyI:C", "polyI:C polynucleotide" or "polyI:C polynucleotide adjuvant" is a double- or single-stranded polynucleotide molecule (RNA or DNA or a combination of DNA and RNA), each strand of which contains at least 6 contiguous inosinic or cytidylic acid residues, or 6 contiguous residues selected from inosinic acid and cytidylic acid in any order (e.g. IICIIC or ICICIC), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 26, 28, 30, 35, 40, 45, 50, 55, 60, 65, 70, 75, 80, 85, 90, 95, 100, 150, 200, 250, 300, 500, 1000 or more residues. Preferred polyI:C polynucleotides may have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a double-stranded polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more preferably, no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

In some embodiments, the polyI:C polynucleotide adjuvant is a traditional form of polyI:C with an approximate molecular weight of 989,486 Daltons, containing a mixture of varying strand lengths of polyI and polyC of several hundred base pairs (Thermo Scientific; USA).

In some embodiments, the compositions as disclosed herein may comprise an adjuvant that activates or increases the activity of TLR2. As used herein, an adjuvant which "activates" or "increases the activity" of a TLR2 includes any adjuvant, in some embodiments a lipid-based adjuvant, which acts as a TLR2 agonist. Further, activating or increasing the activity of TLR2 encompasses its activation in any monomeric, homodimeric or heterodimeric form, and particularly includes the activation of TLR2 as a heterodimer with TLR1 or TLR6 (i.e. TLR1/2 or TLR2/6). Exemplary embodiments of an adjuvant that activates or increases the activity of TLR2 include lipid-based adjuvants, such as those described in WO2013/049941.

Thus, in an embodiment, the composition as disclosed herein may comprise a lipid-based adjuvant, such as disclosed for example in WO2013/049941. In an embodiment, the lipid-based adjuvant is PAM$_2$Cys-Ser-(Lys)4 (SEQ ID NO: 3) or PAM$_3$Cys-Ser-(Lys)4 (SEQ ID NO: 3).

In another embodiment, the vaccine composition as disclosed herein may comprise a lipid A mimic or analog adjuvant, such as for example those disclosed in WO2016/109880 and the references cited therein. In a particular embodiment, the adjuvant may be JL-265 or JL-266 as disclosed in WO2016/109880.

Further examples of adjuvants that may be used include, without limitation, chemokines, colony stimulating factors, cytokines, 1018 ISS, aluminum salts, Amplivax, AS04, AS15, ABM2, Adjumer, Algammulin, AS01B, AS02 (SBASA), ASO2A, BCG, Calcitriol, Chitosan, Cholera toxin, CP-870,893, CpG, polyI:C, CyaA, DETOX (RibiImmunochemicals), Dimethyldioctadecylammonium bromide (DDA), Dibutyl phthalate (DBP), dSLIM, Gamma inulin, GM-CSF, GMDP, Glycerol, IC30, IC31, Imiquimod, ImuFact IMP321, IS Patch, ISCOM, ISCOMATRIX, JuvImmune, LipoVac, LPS, lipid core protein, MF59, monophosphoryl lipid A and analogs or mimics thereof, Montanide® IMS1312, Montanide® based adjuvants (e.g. Montanide ISA-51, -50 and -70), OK-432, OM-174, OM-197-MP-EC, ONTAK, PepTel vector system, other palmitoyl based molecules, PLG microparticles, resiquimod, squalene, SLR172, YF-17 DBCG, QS21, QuilA, P1005, Poloxamer, Saponin, synthetic polynucleotides, Zymosan, pertussis toxin.

Accordingly, the compositions herein may comprise one or more pharmaceutically acceptable adjuvants. In some embodiments, at least one of the antigens may be coupled to at least one of the adjuvants.

In some embodiments, the compositions herein may comprise a polyI:C polynucleotide adjuvant, a lipid-based adjuvant, a lipid A mimic or analog, or any combination thereof. In a particular embodiment, the compositions may comprise a combination of a polyI:C polynucleotide adjuvant and a lipid-based adjuvant, such as described in the adjuvanting system disclosed in U.S. Provisional Patent Application No. 62/256,875 filed on Nov. 18, 2015.

The amount of adjuvant used depends on the type and amount of antigen and on the type of adjuvant. One skilled in the art can readily determine the amount of adjuvant needed in a particular application by empirical testing.

In an embodiment, a composition as described herein comprises the lipopeptide adjuvant PAM$_3$Cys-Ser-(Lys)4 (SEQ ID NO: 3).

Emulsifiers

In some embodiments, the compositions disclosed herein may comprise one or more emulsifiers. The emulsifier may be a pure emulsifying agent or a mixture of emulsifying agents. The emulsifier(s) should be pharmaceutically and/or immunologically acceptable.

The use of an emulsifier may be of particular relevance to preparing compositions that are water-free or substantially free of water. For instance, in some embodiments an emulsifier may be used to assist in stabilizing the amphipathic compound, mixture of amphipathic compound and antigen, or the mixture of amphipathic compound, antigen and other vaccine components (e.g. polyI:C and/or lipid-based adjuvant, T-helper epitope, etc.) when the amphipathic compound or mixtures are resuspended into the hydrophobic carrier. The use of an emulsifier may, for example, promote more even distribution of the amphipathic compound or mixture in the hydrophobic carrier.

The emulsifier may be amphipathic and therefore, the emulsifier may include a broad range of compounds. In some embodiments, the emulsifier may be a surfactant, such as for example, a non-ionic surfactant. Examples of emulsifiers which may be used include polysorbates, which are oily liquids derived from polyethylene glycolyatedsorbital, and sorbitan esters. Polysorbates may include, for example, sorbitanmonooleate. Typical emulsifiers are well-known in the art and include, without limitation, mannide oleate (Arlacel™ A), lecithin, Tween™ 80, Spans™ 20, 80, 83 and 85. In an embodiment, the emulsifier for use in the vaccine compositions is mannide oleate.

The emulsifier is generally pre-mixed with the hydrophobic carrier. In some embodiments, a hydrophobic carrier which already contains an emulsifier may be used. For example, a hydrophobic carrier such Montanide™ ISA 51 already contains the emulsifier mannide oleate. In other embodiments, the hydrophobic carrier may be mixed with the emulsifier before combining with the amphipathic compound, mixture of amphipathic compound and antigen, or the mixture of amphipathic compound, antigen and other vaccine components (e.g. polyI:C and/or lipid-based adjuvant, T-helper epitope, etc.).

The emulsifier is used in an amount effective to promote even distribution of the amphipathic compound in the hydrophobic carrier and/or to assist in the formation of structures, assemblies or arrays described herein. Typically, the volume ratio (v/v) of hydrophobic carrier to emulsifier is in the range of about 5:1 to about 15:1, more particularly 10:1.

T-Helper Epitopes

In some embodiments, the compositions disclosed herein may also comprise at least one T-helper epitope or T-helper antigen. This may be particularly relevant to compositions that comprise additional antigens with CTL epitopes, but as described below T-helper epitopes are also implicated in mediating immune responses involving B-cells.

T-helper epitopes are a sequence of amino acids (natural or non-natural amino acids) that have T-helper activity. T-helper epitopes are recognised by T-helper lymphocytes, which play an important role in establishing and maximising the capabilities of the immune system, and are involved in activating and directing other immune cells, such as for example B-cell antibody class switching.

A T-helper epitope can consist of a continuous or discontinuous epitope. Hence not every amino acid of a T-helper is necessarily part of the epitope. Accordingly, T-helper epitopes, including analogs and segments of T-helper epitopes, are capable of enhancing or stimulating an immune response. Immunodominant T-helper epitopes are broadly reactive in animal and human populations with widely divergent MHC types (Celis 1988; Demotz 1989; Chong 1992). The T-helper domain of the subject peptides may have from about 10 to about 50 amino acids, and more particularly about 10 to about 30 amino acids. When multiple T-helper epitopes are present, then each T-helper epitope acts independently.

In some embodiments, the T-helper epitope may form part of an antigen described herein. In particular, if the antigen is of sufficient size, it may contain an epitope that functions as a T-helper epitope. In other embodiments, the T-helper epitope may be a separate molecule from the antigen.

In another embodiment, T-helper epitope analogs may include substitutions, deletions and insertions of from one to about 10 amino acid residues in the T-helper epitope. T-helper segments are contiguous portions of a T-helper epitope that are sufficient to enhance or stimulate an immune response. An example of T-helper segments is a series of overlapping peptides that are derived from a single longer peptide.

In a particular embodiment, the compositions as disclosed herein may comprise as a T-helper epitope or antigen, the modified Tetanus toxin peptide A16L (830 to 844; AQYIKANSKFIGITEL (SEQ ID NO: 10), with an alanine residue added to its amino terminus to enhance stability (Slingluff 2001).

Other sources of T-helper epitopes which may be used in the present compositions include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T-helper epitopes.

In some embodiments, the T-helper epitope may be a universal T-helper epitope. A universal T-helper epitope as used herein refers to a peptide or other immunogenic molecule, or a fragment thereof, that binds to a multiplicity of MHC class II molecules in a manner that activates T cell function in a class II (CD4+ T cells)-restricted manner. An example of a universal T-helper epitope is PADRE (pan-DR epitope) comprising the peptide sequence AKXVAAWTLKAAA (SEQ ID NO: 11), wherein X may be cyclohexylalanyl. PADRE specifically has a CD4+ T-helper epitope, that is, it stimulates induction of a PADRE-specific CD4+ T-helper response.

In addition to the modified tetanus toxin peptide A16L mentioned earlier, Tetanus toxoid has other T-helper epitopes that work in the similar manner as PADRE. Tetanus and diphtheria toxins have universal epitopes for human CD4+ cells (Diethelm-Okita 2000). In another embodiment, the T-helper epitope may be a tetanus toxoid peptide such as F21E comprising the peptide sequence FNNFTVSFWLRVPKVSASHLE (amino acids 947-967; SEQ ID NO: 12).

In certain embodiments, the T-helper epitope is fused to at least one of the one or more antigens in the composition as disclosed herein (e.g. a fusion peptide).

Water-Free Embodiments of the Compositions

In an embodiment, the compositions disclosed herein are water-free or substantially free of water, i.e. the compositions are not emulsions.

By "water-free" it is meant that the compositions contain no water at all. In another embodiment, the compositions may be substantially free of water. The term "substantially free of water" is intended to encompass embodiments where the hydrophobic carrier may still contain small quantities of water, provided that the water is present in the non-continuous phase of the carrier. For example, individual components of the composition may have small quantities of bound water that may not be completely removed by processes such as lyophilization or evaporation and certain hydrophobic carriers may contain small amounts of water dissolved therein. Generally, compositions as disclosed herein that are "substantially free of water" contain, for example, less than about 10%, 9%, 8%, 7%, 6%, 5%, 4%, 3%, 2%, 1%, 0.5%, 0.1%, 0.05% or 0.01% water on a weight/weight basis of the total weight of the carrier component of the composition. The compositions that still contain small quantities of water do not contain a sufficient amount of water such that an emulsion would be formed.

Without being held to any particular theory of action, it is thought that when a water-free composition of the present disclosure is used, the formulation creates a strong depot that persists over several weeks allowing prolonged clearance of antigen and interaction of the vaccine with the immune system. In this regard, it has been reported that lipid-in-oil based formulations achieve peak clearance within 3 weeks of immunization, and clearance continues at a slower rate over six months (Brewer 2014). This is in contrast to aqueous vaccine formulations which release antigens quickly over a few hours to a week; or emulsions which form a short-lived depot.

Methods for Preparing the Compositions

The compositions may be prepared by known methods in the art having regard to the present disclosure. Exemplary embodiments for preparing the compositions disclosed herein are described below, including in the examples, without limitation.

As used in this section, the terms "antigen" and "adjuvant" are used generally to describe how an antigen and adjuvant may be formulated in the compositions of the present disclosure. The term "antigen" encompasses both the singular form "antigen" and the plural "antigens". Likewise, the term "adjuvant" encompasses both the singular form "adjuvant" and the plural "adjuvants". It is not necessary that all antigens and adjuvants be introduced into the vaccine composition in the same way.

In an embodiment for preparing the composition, the antigen and optionally other components (e.g. adjuvant, T-helper epitope, etc.) are reconstituted in a suitable solvent together with an amphipathic compound. The components are then dried to form a dry cake, and the dry cake is resuspended in a hydrophobic carrier. The step of drying may be performed by various means known in the art, such as by freeze-drying, lyophilization, rotary evaporation, evaporation under pressure, etc. Low heat drying that does not compromise the integrity of the components can also be used. Heat can also be used to assist in resuspending the antigen/amphipathic compound mixture.

The "suitable solvent" is one that is suitable for solubilizing the antigen, adjuvant and/or amphipathic compound, and can be determined by the skilled person. In an embodiment, sodium phosphate buffer (0.2M, pH 6.0) or sodium phosphate buffer (0.1M, pH 7.0) may be used. In another embodiment, a polar protic solvent such as an alcohol (e.g. tert-butanol, n-butanol, isopropanol, n-propanol, ethanol or methanol), water, acetate buffer, formic acid or chloroform may be used. In some cases, the same solvent can be used to solubilize each of the amphipathic compound, antigen and adjuvant, and the solubilized components are then mixed. Alternatively, the antigen, adjuvant and amphipathic compound may be mixed prior to solubilization, and then solubilized together. In a further alternative, only one or more of the amphipathic compound, antigen or adjuvant are solubilized, and the non-solubilized component(s) are added.

In a particular embodiment, to prepare the compositions the antigen and adjuvant are reconstituted together or separately in sodium phosphate buffer with S100 lipids and cholesterol (Lipoid, Germany). These components are then lyophilized to form a dry cake. Just prior to injection, the dry cake is resuspended in ISA51 VG oil (SEPPIC, France) to prepare a water-free oil-based composition.

In another embodiment, to prepare the compositions the antigen and adjuvant are reconstituted together or separately in sodium phosphate buffer with DOPC and cholesterol (Lipoid, Germany). These components are then lyophilized to form a dry cake. Just prior to injection, the dry cake is resuspended in ISA51 VG oil (SEPPIC, France) to prepare a water-free oil-based composition.

In another embodiment, to prepare the compositions the antigen is mixed with synthetic lipid/cholesterol nanoparticles (size≤110 nm) and adjuvant in sodium phosphate buffer (100 mM, pH 6.0). The synthetic lipid may be DOPC. The components are then lyophilized to form a dry cake. Just prior to injection, the dry cake is resuspended in ISA51 VG oil (SEPPIC, France) to prepare a water-free oil-based composition.

In each of the embodiments described above, the antigen may be dimerized beforehand by dissolving the antigen in a mixture of 10% DMSO/0.5% acetic acid in water (w/w) and heating overnight at 37° C.

In a particular embodiment, the compositions may be prepared by:
preparing dimerized antigen by dissolving the antigen in a mixture of 10% DMSO/0.5% acetic acid in water (w/w) and heating overnight at 37° C.;
preparing a sized lipid mixture with synthetic lipid/cholesterol nanoparticles of size≤110 nm;
mixing dimerized antigen with the synthetic lipid/cholesterol nanoparticles and adjuvant in sodium phosphate buffer (100 mM, pH 6.0);
lyophilizing the mixture to form a dry cake; and
resuspending the dry cake in a hydrophobic carrier In the above embodiments, without being bound to a particular theory of action, it is believed that removal (drying) of the solvent leaves the components, including the antigen, in an array of amphipathic compound molecules with their hydrophilic head groups oriented towards the vaccine components. The vaccine components and amphipathic compound can then be suspended in the hydrophobic carrier (such as oil) in the absence of water, since they have been made sufficiently hydrophobic.

Additional components as described herein, such as T-helper epitope, may be added at any stage in the formulation process. For instance, one or more such additional components may be combined with the antigen, adjuvant and/or amphipathic compound either before or after solubilization, or added to the solubilized mixture. In another embodiment, the additional components may instead be added to or combined with the dried mixture of antigen, adjuvant and amphipathic compound, or combined with the hydrophobic carrier either before or after resuspension of the dry mixture of antigen, adjuvant and amphipathic compound in the hydrophobic carrier. In an embodiment, the T-helper epitope is added to the composition in the same way as the antigen. In an embodiment, the antigen and T-helper epitope are a fused peptide.

In some embodiments, it may be appropriate to include an emulsifier in the hydrophobic carrier to assist in stabilizing the components of the dry cake when they are resuspended in the hydrophobic carrier. The emulsifier is provided in an amount sufficient to resuspend the dry mixture of antigen, adjuvant and amphipathic compound in the hydrophobic carrier and maintain the antigen, adjuvant and amphipathic compound in suspension in the hydrophobic carrier. For example, the emulsifier may be present at about 5% to about 15% weight/weight or weight/volume of the hydrophobic carrier.

Stabilizers such as sugars, anti-oxidants, or preservatives that maintain the biological activity or improve chemical stability to prolong the shelf life of any of the components, may be added to the compositions.

Immune Responses and Treatment Indications

The present disclosure relates to methods for inducing an antibody immune response in a human subject using a low dose volume of a composition comprising an antigen comprising a B-cell epitope as described herein, corresponding uses, and compositions and kits which may be used in such methods.

As referred to herein, the expression "immune response" refers to an antibody immune response, unless specified otherwise.

An "antibody immune response" or "humoral immune response" (used interchangeably herein), as opposed to cell-mediated immunity, is mediated by secreted antibodies which are produced in the cells of the B lymphocyte lineage (B-cells). Such secreted antibodies bind to antigens, such as for example those on the surfaces of foreign substances, pathogens (e.g. viruses, bacteria, etc.) and/or cancer cells, and flag them for destruction.

As used herein, "humoral immune response" refers to antibody production and may also include, in addition or alternatively, the accessory processes that accompany it, such as for example the generation and/or activation of T-helper 2 (Th2) or T-helper 17 (Th17) cells, cytokine production, isotype switching, affinity maturation and memory cell activation. "Humoral immune response" may also include the effector functions of an antibody, such as for example toxin neutralization, classical complement activation, and promotion of phagocytosis and pathogen elimination. The humoral immune response is often aided by CD4+ Th2 cells and therefore the activation or generation of this cell type may also be indicative of a humoral immune response. The term "humoral immune response" is used interchangeably herein with "antibody response" or "antibody immune response".

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B-cells). Engagement of antigen with antibody expressed on the surface of B-cells can induce an antibody response comprising stimulation of B-cells to become activated, to undergo mitosis and to terminally differentiate into plasma cells, which are specialized for synthesis and secretion of antigen-specific antibody.

B-cells are the sole producers of antibodies during an immune response and are thus a key element to effective humoral immunity. In addition to producing large amounts of antibodies, B-cells also act as antigen-presenting cells and can present antigen to T cells, such as T helper CD4 or cytotoxic CD8+ T cells, thus propagating the immune response. B-cells, as well as T cells, are part of the adaptive immune response. During an active immune response, induced for example by either vaccination or natural infection, antigen-specific B-cells are activated and clonally expand. During expansion, B-cells evolve to have higher affinity for the epitope. Proliferation of B-cells can be induced indirectly by activated T-helper cells, and also directly through stimulation of receptors, such as the TLRs.

Antigen presenting cells, such as dendritic cells and B-cells, are drawn to vaccination sites and can interact with antigens and adjuvants contained in a vaccine composition. Typically, the adjuvant stimulates the cells to become activated and the antigen provides the blueprint for the target. Different types of adjuvants may provide different stimulation signals to cells. For example, poly I:C (a TLR3 agonist) can activate dendritic cells, but not B-cells. Adjuvants such as Pam3Cys, Pam2Cys and FSL-1 are especially adept at activating and initiating proliferation of B-cells, which is expected to facilitate the production of an antibody response (Moyle 2008; So 2012).

A humoral immune response is one of the common mechanisms for effective infectious disease vaccines (e.g. to protect against viral or bacterial invaders). However, a humoral immune response can also be useful for combating cancer. Whereas a cancer vaccine is typically designed to produce a cell-mediated immune response that can recognize and destroy cancer cells, B-cell mediated responses may target cancer cells through other mechanisms which may in some instances cooperate with a cytotoxic T cell for maximum benefit. Examples of B-cell mediated (e.g. humoral immune response mediated) anti-tumor responses include, without limitation: 1) Antibodies produced by B-cells that bind to surface antigens found on tumor cells or other cells that influence tumorigenesis. Such antibodies can, for example. induce killing of target cells through antibody-dependent cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with a tumor or tumor-associated cells to modulate a signaling or cellular pathway that supports cancer; and 4) Antibodies that bind to intracellular targets and mediate anti-tumor activity through a currently unknown mechanism.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Without limitation, other assays that may be used to detect the presence of an antigen-specific antibody include immunological assays (e.g. radioimmunoassay (RIA)), immunoprecipitation assays, and protein blot (e.g. Western blot) assays; and neutralization assays (e.g. neutralization of viral infectivity in an in vitro or in vivo assay).

The methods and compositions described herein may be useful for treating or preventing diseases and/or disorders ameliorated by a humoral immune response. The methods and compositions may find application in any instance in which it is desired to administer an antigen to a subject to induce a humoral immune response.

In some embodiments, the methods disclosed herein may be for the treatment and/or prevention of a disease caused by a bacteria, a virus, a fungus, a parasite, an allergen, or a tumor cell that expresses the antigen.

"Treating" or "treatment of", or "preventing" or "prevention of", as used herein, refers to an approach for obtaining beneficial or desired results. Beneficial or desired results may include, but are not limited to, alleviation or amelioration of one or more symptoms or conditions, diminishment of extent of disease, stabilisation of the state of disease, prevention of development of disease, prevention of spread of disease, delay or slowing of disease progression (e.g. suppression), delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily or preventing the occurrence of disease, such as by preventing infection in a subject. "Treating" may also refer to a reduction in the size of a tumor mass, reduction in tumor aggressiveness, etc.

"Treating" may be distinguished from "preventing" in that "treating" typically occurs in a subject who already has a disease or disorder, or is known to have already been exposed to an infectious agent, whereas "preventing" typically occurs in a subject who does not have a disease or disorder, or is not known to have been exposed to an infectious agent. As will be appreciated, there may be overlap in treatment and prevention. For example, it is possible to be "treating" a disease in a subject, while at same time "preventing" symptoms or progression of the disease. Moreover, at least in the context of vaccination, "treating" and "preventing" may overlap in that the treatment of a subject is to induce an immune response that may have the subsequent effect of preventing infection by a pathogen or preventing the underlying disease or symptoms caused by infection with the pathogen. These preventive aspects are encompassed herein by expressions such as "treatment of an infectious disease".

In an embodiment, the methods and compositions disclosed herein may be used for treating and/or preventing an infectious disease in a human subject, such as caused by a viral infection. The subject may be infected with a virus or may be at risk of developing a viral infection.

Viral infections that may be treated and/or prevented by the low dose volume methods disclosed herein include, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus (HPV), Parvovirus, Hepatitis A virus, Hepatitis B virus, Hepatitis C virus, Human immunodeficiency virus, Orthoreovirus, Rotavirus, Ebola virus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella. In a particular embodiment, the viral infection is Human papillomavirus, Ebola virus, Human respiratory syncytial virus or an influenza virus.

In an embodiment, the methods disclosed herein may be used for the treatment and/or prevention of a lower respiratory infection in a human subject, wherein the infection is caused by a respiratory syncytial virus (RSV). In an embodiment, the infection is caused by an RSV subgroup A virus strain. In an embodiment, the infection is caused by an RSV subgroup B virus strain.

In another embodiment, the methods or compositions disclosed herein may be used for treating and/or preventing an infectious disease, such as caused by a non-viral pathogen (such as a bacterium or protozoan) in a human subject in need thereof. The subject may be infected with the pathogen or may be at risk of developing an infection by the pathogen. Without limitation, exemplary bacterial pathogens may include Anthrax (*Bacillus anthracis*), *Brucella, Bordetella pertussis, Candida, Chlamydia pneumoniae, Chlamydia psittaci*, Cholera, *Clostridium botulinum*, Coccidioidesimmitis, *Cryptococcus*, Diphtheria, *Escherichia coli* O157: H7, Enterohemorrhagic *Escherichia coli*, Enterotoxigenic *Escherichia coli, Haemophilus influenzae, Helicobacter pylori, Legionella, Leptospira, Listeria*, Meningococcus, *Mycoplasma pneumoniae, Mycobacterium*, Pertussis, Pneumonia, *Salmonella, Shigella, Staphylococcus, Streptococcus pneumoniae* and *Yersinia enterocolitica*. In a particular embodiment, the bacterial infection is Anthrax. Without limitation, exemplary protozoan pathogens may include those of the genus *Plasmodium* (*Plasmodium falciparum, Plasmodium malariae, Plasmodium vivax, Plasmodium ovale* or *Plasmodium knowlesi*), which cause malaria.

In an embodiment, the methods and compositions disclosed herein may be used for treating cancer in a human subject in need thereof. In an embodiment, the cancer is one that expresses a membrane surface-bound cancer antigen that is capable of being recognized by an antibody.

As used herein, the terms "cancer", "cancer cells", "tumor" and "tumor cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

Without limitation, cancers that may be capable of being treated and/or prevented by the use or administration of a composition as disclosed herein include carcinoma, adenocarcinoma, lymphoma, leukemia, sarcoma, blastoma, myeloma, and germ cell tumors. Without limitation, particularly suitable embodiments may include glioblastoma, multiple myeloma, ovarian cancer, breast cancer, fallopian tube cancer, prostate cancer or peritoneal cancer. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. In another embodiment, the cancer may be one that expresses one or more cancer-specific antigens (e.g. survivin).

In a particular embodiment, the cancer is breast cancer, ovarian cancer, prostate cancer, fallopian tube cancer, peritoneal cancer, glioblastoma or diffuse large B cell lymphoma.

In another embodiment, the methods or compositions disclosed herein may be used for treating and/or preventing a neurodegenerative disease in a subject in need thereof, wherein the neurodegenerative disease is associated with the expression of an antigen. The subject may have a neurodegenerative disease or may be at risk of developing a neurodegenerative disease. Neurodegenerative diseases that may be treated and/or prevented by the methods or compositions disclosed herein include, without limitation, Alzheimer's disease, Parkinson's disease, Huntington's disease, and amyotrophic lateral sclerosis (ALS).

In another embodiment, the methods or compositions disclosed herein may be used for treating and/or preventing an addiction disease (such as, for example, addiction to cocaine).

In another embodiment, the methods or compositions disclosed herein may be used for neutralizing a toxin, virus, bacterium or allergen, with an antibody, said method comprising administering the composition as described herein to a subject. For example, antibodies produced in response to the antigen in the vaccine may neutralize or sequester the toxin, virus, bacterium or allergen. In an embodiment, the toxin is a drug substance such as, for example, cocaine.

Kits, Combinations and Reagents

The compositions disclosed herein are optionally provided to a user as a kit. For example, a kit of the present disclosure contains one or more components of the compositions disclosed herein. The kit can further comprise one or more additional reagents, packaging material, containers for holding the components of the kit, and an instruction set or user manual detailing preferred methods of using the kit components. In an embodiment, the containers are vials.

In an embodiment, the kit contains pre-formulated vaccine in a container in a ready-to-use format. As an example, in an embodiment, the kit comprises at least one container comprising an amphipathic compound, an antigen and a hydrophobic carrier. The pre-formulated vaccine may further comprise an adjuvant or any other additional components.

In an alternative embodiment of the kit, the vaccine may be provided with all components, except hydrophobic carrier, in one container (e.g. as a dry cake) ready for reconstitution in the hydrophobic carrier or as individual components in separate containers for formulation, lyophilization and reconstitution in the hydrophobic carrier.

In an embodiment, the kit may comprise a first container comprising an amphipathic compound and an antigen; and a second container comprising a hydrophobic carrier. In this embodiment, the vaccine components in the first container may be in the form of a dry cake that is ready to be re-suspended in the hydrophobic carrier.

In an embodiment, the kit may comprise (i) a first vial containing the antigen, adjuvant and phospholipids in a dry lyophilized powder, and (ii) a second vial containing the hydrophobic carrier, which serves as a diluent.

In various aspects of the above kit embodiments, in addition to antigen, amphipathic compound and hydrophobic carrier, the vaccine may optionally further comprise one or more of an adjuvant, a T-helper epitope and an emulsifier. These components may be provided individually in separate containers or may be provided as any combination thereof together in a container, such as together in a container with the antigen and amphipathic compound.

In an embodiment of the kit, the antigen is a peptide antigen comprising the ectodomain of the small hydrophobic protein (SHe) of a subgroup A or subgroup B human RSV strain. For example, in an embodiment, the antigen comprises or consists of the amino acid sequence NKLCEYNVFHNKTFELPRARVNT (SEQ ID NO: 1).

In an embodiment of the kit, the adjuvant is PAM$_3$Cys-Ser-(Lys)4 (SEQ ID NO: 3).

In an embodiment of the kit, the amphipathic compound is one or more lipids, such as phospholipids. In an embodiment, the lipids are 1,2-dioleoyl-sn-glycero-3-phosphocholine (DOPC) and cholesterol.

In an embodiment of the kit, the hydrophobic carrier is Montanide® ISA 51 VG.

Thus, in an embodiment, the kit comprises two vials with contents as detailed below:

| Vials | Component |
|---|---|
| Vial 1 | (lyophilized cake) in a sterile 2 mL clear borosilicate glass vial |
| Lipid mixture | Phosphotidyl choline: DOPC synthetic lipid (GMP grade) Cholesterol: Sheep's wool, high purity, non-BSE countrites (GMP grade) |
| Adjuvant | Short synthetic lipopeptide(PAM₃Cys-Ser-(Lys)4; SEQ ID NO: 3) (GMP grade) |
| Antigen | 23 amino acid peptide from the ecto-domain of the RSV small hydrophobic protein (SHe) classified as SHe A peptide (NKLCEYNVFHNKTFELPRARVNT; SEQ ID NO: 1) (GMP grade) |
| Vial 2 | (oil diluent) in a sterile 5 mL amber borosilicate glass vial |
| Hydrophobic carrier (oil diluent) | Montanide ISA 51 VG (GMP grade) |

The skilled person will appreciate that alternate arrangements of the kit are possible and are encompassed by the disclosure herein.

The kit as disclosed herein may be used in practicing the methods disclosed herein. In an embodiment, the kit is for use in inducing an antibody immune response to the antigen in a human subject using a low dose volume of the composition in the kit. In an embodiment, the kit is for preparing a composition that is water-free or substantially free of water.

Embodiments

Particular embodiments of the present disclosure include, without limitation, the following:

(1) A method for inducing an antibody immune response in a human subject, comprising administering parenterally to the human subject a low dose volume of a composition comprising:
an antigen comprising a B-cell epitope;
an amphipathic compound; and
a hydrophobic carrier,
wherein the low dose volume of the composition is less than 100 μl and induces an antibody immune response to the B-cell epitope in the human subject.

(2) The method of paragraph (1), wherein the low dose volume is about 50 μl, about 60 μl, about 70 μl, about 80 μl or about 90 μl.

(3) The method of paragraph (1) or (2), wherein the low dose volume is between about 50 μl to about 75 μl.

(4) The method of any one of paragraphs (1) to (3), wherein the low dose volume is about 50 μl.

(5) The method of any one of paragraphs (1) to (4), wherein the composition comprises about 5 μg, about 10 μg, about 15 μg, about 20 μg, about 25 μg, about 30 μg, about 35 μg, about 40 μg, about 45 μg, or about 50 μg of the antigen.

(6) The method of paragraph (5), wherein the composition comprises about 10 μg or about 25 μg of the antigen.

(7) The method of any one of paragraphs (1) to (6), comprising administering only a single priming administration and a single booster administration of the composition.

(8) The method of paragraph (7), wherein the single booster administration is provided to the human subject about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, or more after the single priming administration.

(9) The method of paragraph (7) or (8), wherein the single booster administration is provided to the human subject about 56 days after the single priming administration.

(10) The method of any one of paragraphs (1) to (6), comprising administering only a single administration of the composition.

(11) The method of any one of paragraphs (1) to (10), further comprising administering to the human subject, after at least one administration of the low dose volume of the composition, a subsequent dose of the antigen formulated in an aqueous composition that does not comprise the hydrophobic carrier or does not comprise the hydrophobic carrier and the amphipathic compound.

(12) The method of any one of paragraphs (1) to (11), wherein the antibody immune response induced by the low dose volume of the composition is detectable in the human subject at least as early as 28 days after a first administration of the composition.

(13) The method of any one of paragraphs (1) to (12), wherein the antibody immune response induced by the low dose volume of the composition persists at least for 84 days after a first administration of the composition.

(14) The method of any one of paragraphs (1) to (13), wherein the antibody immune response induced by the low dose volume of the composition persists at least for 236 days after a first administration of the composition.

(15) The method of any one of paragraphs (1) to (14), wherein the low dose volume of the composition induces an antibody immune response in at least 75%, at least 80%, at least 85%, at least 90%, at least 95% or at least 100% of treated human subjects by day 56, day 84 or day 236 post-administration.

(16) The method of paragraph (15), wherein the low dose volume of the composition induces an antibody immune response in 100% of treated human subjects at least by day 84 or day 236 post-administration.

(17) The method of any one of paragraphs (1) to (16), wherein the antibody immune response induced by the low dose volume of the composition is enhanced as compared to the antibody immune response induced in human subjects administered the antigen formulated in an alum composition, wherein the alum composition comprises the antigen, an alum adjuvant, a mineral adjuvant (e.g. Alhydrogel), and an aqueous carrier.

(18) The method of paragraph (17), wherein the enhancement in the antibody immune response is an increase in the percentage of human subjects that have a detectable antigen-specific antibody immune response to the antigen and/or an increase in the average antigen-specific antibody endpoint titer.

(19) The method of paragraph (18), wherein each of the composition and the alum composition comprise 10 μg of the antigen and the average antigen-specific antibody endpoint titer with the composition is: (i) at least about 123.2 times higher than the alum composition at day 28 post-administration; and/or (ii) at least about 16.7 times higher than the alum composition at day 56.

(20) The method of paragraph (18), wherein each of the composition and the alum composition comprise 25 μg of the antigen and the average antigen-specific antibody endpoint titer for the composition is: (i) at least about 35.3 times higher than the alum composition at day 28 post-administration; and/or (ii) at least about 13.1 times higher than the alum composition at day 56.

(21) The method of paragraph (18), wherein each of the composition and the alum composition comprise 10 μg of the antigen and the percentage of human subjects that have a detectable antigen-specific antibody immune response when treated with the composition is at least about 2.0 times higher than with the alum composition, at day 56 post-administration.

(22) The method of paragraph (18), wherein each of the composition and the alum composition comprise 25 μg of the antigen and the percentage of human subjects that have a detectable antigen-specific antibody immune response when treated with the composition is at least about 5.0 times higher than with the alum composition, at day 56 post-administration.

(23) The method of any one of paragraphs (17) to (22), wherein the composition has an acceptable safety profile in respect of total solicited systemic adverse events and/or total unsolicited adverse events.

(24) The method of any one of paragraphs (1) to (23), wherein the human subject is an infant, an adolescent, an adult, or an elderly subject.

(25) The method of paragraph (24), wherein the human subject is 0-2 years, 50-64 years, or over 65 years of age.

(26) The method of any one of paragraphs (1) to (25), wherein the composition further comprises an adjuvant.

(27) The method of paragraph (26), wherein the adjuvant is a polyI:C polynucleotide adjuvant, a lipid-based adjuvant, a lipid A mimic or analog thereof, or any combination thereof.

(28) The method of paragraph (27), wherein the lipid-based adjuvant is a lipopeptide, for example PAM$_2$Cys-Ser-(Lys)4 (SEQ ID NO: 3) or PAM$_3$Cys-Ser-(Lys)4 (SEQ ID NO: 3).

(29) The method of any one of paragraphs (1) to (28), wherein the antigen is a peptide antigen of 5 to 50 amino acids in length or a polynucleotide encoding the peptide antigen.

(30) The method of any one of paragraphs (1) to (29), wherein the antigen is a synthetic peptide antigen that is naturally weakly immunogenic in the human subject.

(31) The method of any one of paragraphs (1) to (30), wherein the antigen is: (i) derived from a virus, bacterium or protozoan, such as for example Ebola virus, Zika virus, human papillomavirus (HPV), influenza virus, respiratory syncytial virus, *Bordetella pertussis*, *Bacillus anthracis* or *Plasmodium malariae*; (ii) a membrane surface-bound cancer antigen, such as for example a survivin antigen; (iii) a toxin, such as for example cocaine; or (iv) a neoantigen.

(32) The method of any one of paragraphs (1) to (31), wherein the antigen comprises or consists of the small hydrophobic protein (SH) of a virus or a fragment thereof.

(33) The method of paragraph (32), wherein the virus is a paramyxovirus.

(34) The method of paragraph (33), wherein the paramyxovirus is a Respiratory Syncytial Virus (RSV), for example a human RSV.

(35) The method of any one of paragraphs (32) to (34), wherein the antigen comprises or consists of the ectodomain of the SH (SHe) or a fragment thereof.

(36) The method of paragraph (35), wherein the SHe is derived from a subgroup A human RSV strain or a subgroup B human RSV strain.

(37) The method of paragraph (36), wherein the SHe comprises the amino acid sequence NKLCEYNVFHNKTFELPRARVNT (SEQ ID NO: 1) or NKLSEHKTFCNKTLEQGQMYQINT (SEQ ID NO: 2), or an amino acid sequence that is at least 75% identical to SEQ ID NO: 1 or 2.

(38) The method of paragraph (37), wherein the antigen comprises or consists of the amino acid sequence NKLCEYNVFHNKTFELPRARVNT (SEQ ID NO: 1), NKLSEYNVFHNKTFELPRARVNT (SEQ ID NO: 6), NKLSEHKTFCNKTLEQGQMYQINT (SEQ ID NO: 2), or a fragment thereof.

(39) The method of paragraph (38), wherein the antigen consists of the amino acid sequence NKLCEYNVFHNKTFELPRARVNT (SEQ ID NO: 1).

(40) The method of any one of paragraphs (35) to (39), wherein the SHe is presented as an oligomer, for example a dimer.

(41) The method of any one of paragraphs (35) to (40), wherein the SHe is genetically or chemically linked to a carrier.

(42) The method of paragraph (41), wherein the carrier is the amphipathic compound or a structure formed therefrom.

(43) The method of any one of paragraphs (31) to (42), comprising administering the low dose volume of the composition to the human subject prior to exposure of the human subject to the virus, bacterium, protozoan or toxin.

(44) The method of any one of paragraphs (1) to (43), wherein the antigen is sufficiently hydrophobic, or is made sufficiently hydrophobic, such that the antigen is miscible in the hydrophobic carrier.

(45) The method of paragraph (44), wherein the antigen is made sufficiently hydrophobic by the presence of the amphipathic compound in the composition.

(46) The method of any one of paragraphs (1) to (45), wherein the amphipathic compound is a lipid or a lipid mixture.

(47) The method of paragraph (46), wherein the lipid or lipid mixture comprises a phospholipid, for example phosphatidylcholine, dioleoyl phosphatidylcholine (DOPC), lecithin (e.g. Lipoid S100) or a mixture thereof.

(48) The method of paragraph (46) or (47), wherein the amphipathic compound is a lipid mixture of dioleoyl phosphatidylcholine (DOPC) and cholesterol.

(49) The method of any one of paragraphs (46) to (48), wherein the lipids form a sheet or vesicular structure, partially or completely surrounding the antigen.

(50) The method of any one of paragraphs (46) to (48), wherein the lipids form a closed vesicular structure around the antigen, for example a single layer vesicular structure (e.g. a micelle) or a bilayer vesicular structure (e.g. a unilamellar or multilamellar liposome).

(51) The method of any one of paragraphs (1) to (50), wherein the hydrophobic carrier is an oil or a mixture of oils.

(52) The method of paragraph (51), wherein the hydrophobic carrier comprises a vegetable oil, nut oil, mineral oil, or a mixture thereof.

(53) The method of paragraph (52), wherein the hydrophobic carrier is mineral oil or is a mannide oleate in mineral oil solution, for example Montanide® ISA 51 VG.

(54) The method of any one of paragraphs (1) to (53), wherein the composition comprises:
a peptide comprising the amino acid sequence

```
                                      (SEQ ID NO: 1)
NKLCEYNVFHNKTFELPRARVNT;
``` a lipid mixture comprising dioleoyl phosphatidylcholine (DOPC) and cholesterol;

a short synthetic lipopeptide which is PAM₃Cys-Ser-(Lys)4 (SEQ ID NO: 3); and

Montanide® ISA 51 VG.

(55) The method of any one of paragraphs (1) to (54), wherein the composition is water-free or substantially free of water.

(56) The method of paragraph (55), wherein a composition that is substantially free of water comprises less than about 10%, 9%, 8%, 7%, 6%, 5%, 4%, 3%, 2%, 1%, 0.5%, 0.1%, 0.05% or 0.01% water on a weight/weight basis of the total weight of the carrier.

(57) The method of any one of paragraphs (1) to (56), comprising administering the low dose volume of the composition by injection.

(58) The method of paragraph (57), comprising injecting the low dose volume of the composition intramuscularly.

(59) The method of any one of paragraphs (1) to (58), which is for the treatment or prevention of an infectious disease in the human subject.

(60) Use of a low dose volume of a composition comprising:

an antigen comprising a B-cell epitope;
an amphipathic compound; and
a hydrophobic carrier, for inducing an antibody immune response to the B-cell epitope in a human subject, wherein the composition is for administration parenterally and the low dose volume of the composition is less than 100 µl.

(61) The use according to paragraph (60), wherein: the low dose volume is as defined in any one of paragraphs (2) to (4); the quantity of antigen is as defined in paragraph (5) or (6); the composition is for administration as defined in any one of paragraphs (7) to (11), (43), (57) and (58); the antibody immune response is as defined in any one of paragraphs (12) to (22); the use provides a safety profile as defined in paragraph (23); the human subject is as defined in paragraph (24) or (25); the composition further comprises an adjuvant as defined in any one of paragraphs (26) to (28); the antigen is as defined in any one of paragraphs (29) to (42), (44) and (45); the amphipathic compound is as defined in any one of paragraphs (46) to (50); the hydrophobic carrier is as defined in any one of paragraphs (51) to (53); and/or the composition is as defined in any one of paragraphs (54) to (56).

(62) The use according to paragraph (60) or (61), which is for the treatment or prevention of an infectious disease in a human subject, for example the treatment or prevention of RSV.

(63) A composition or kit for use in the method according to any one of paragraphs (1) to (59).

The invention is further illustrated by the following non-limiting examples.

EXAMPLES

Clinical Trial Protocol

A phase 1 study, designated CI1204, conducted in Canada (NCT # 02472548) evaluated the safety and immune potency of low dose volume administrations of an oil-based formulation compared to an alum-based formulation to induce immune responses towards a Respiratory Syncytial Virus (RSV) small hydrophobic ectodomain group A (SHe A) peptide antigen. The study was a randomized, observer-blind, placebo-controlled, dose escalation trial. The study involved two steps, the first step evaluated a low peptide dose formulation and the second step evaluated a high peptide dose formulation.

RSV SHe A peptide antigen (NKLCEYNVFHNKTFEL-PRARVNT; SEQ ID NO: 1) used in this study was synthesized by PolyPeptide (San Diego, USA). The peptide was dimerized by dissolving the RSV SHe A peptide antigen (10 milligrams per milliliter) in a mixture of 10% DMSO/0.5% acetic acid in water (w/w) and heating at 37° C. overnight. The oil-based vaccine used in this study consisted of the RSV SHe A peptide antigen at 0.2 milligrams per milliliter (low peptide) or 0.5 milligrams per milliliter (high peptide). Both the low and high peptide oil-based vaccines also contained lipopeptide adjuvant at 0.04 milligrams per milliliter (PAM₃Cys-Ser-(Lys)4; SEQ ID NO: 3; PolyPeptide, San Diego, USA), synthetic 1,2-dioleoyl-sn-glycero-3-phosphocholine lipid at 120 milligrams per milliliter (DOPC; Lipoid, GmbH, Germany) and cholesterol at 12 milligrams per milliliter (Lipoid, GmbH, Germany). The vaccine was delivered in ISA 51 VG oil (SEPPIC, France). To formulate the oil-based vaccine, the dimerized RSV SHe A peptide antigen was mixed (at high or low peptide) with synthetic lipid/cholesterol nanoparticles (size≤110 nm) and lipopeptide adjuvant in sodium phosphate buffer (100 millimolar, pH 6.0). The vaccine components were then lyophilized to form a dry cake. Just prior to injection, the dry cake was resuspended in oil.

The reconstituted composition was as follows:

| Reconstituted Vaccine | Component | Concentration |
|---|---|---|
| Lipid mixture | Phosphotidyl choline: DOPC synthetic lipid (GMP grade) | 120 mg/mL |
|  | Cholesterol: Sheep's wool, high purity, non-BSE countrites (GMP grade) | 12 mg/mL |
| Adjuvant | Short synthetic lipopeptide (GMP grade) | 0.04 mg/mL |
| Antigen | 23 amino acid peptide from the ectodomain of the RSV small hydrophobic protein (SHe) classified as SHe A peptide (NKLCEYNVFHNKTFEL-PRARVNT; SEQ ID NO: 1) (GMP grade) | 0.5 mg/mL in DPX-RSV(A) high peptide<br>0.2 mg/mL in DPX-RSV(A) low peptide |

| Reconstituted Vaccine | Component | Concentration |
|---|---|---|
| Hydrophobic carrier (oil diluent) | Montanide ISA 51 VG | 0.45 mL |

The alum-based vaccine used in this study consisted of the RSV SHe A peptide antigen at 0.2 milligrams per milliliter (low peptide) or 0.5 milligrams per milliliter (high peptide). Both the low and high peptide alum-based vaccines also contained Alhydrogel® 2% at 10 milligrams of Aluminium per milliliter (Brenntag Biosector A/S, Denmark). To formulate the alum-based vaccine, the dimerized RSV SHe A peptide antigen was diluted with sodium acetate buffer (10 millimolar, pH 7.0) and filled into vials. Just prior to injection, the vaccine was mixed with Alhydrogel® 2% (high peptide) at 1 milligram of Aluminium per milliliter of vaccine product or Alhydrogel® 2%/water (low peptide).

The reconstituted alum composition was as follows:

| Alum vaccine | Component | Concentration |
|---|---|---|
| Antigen | 23 amino acid peptide from the hydrophobic protein (SHe) classified as SHe A peptide (NKLCEYNVFHNKTFELPRARVNT; SEQ ID NO: 1) (GMP grade) ectodomain of the RSV small | 0.5 mg/mL in RSV(A)-Alum high peptide 0.2 mg/mL in RSV(A)-Alum low peptide |
| Mineral Adjuvant | Alhyrdogel (GMP grade) | 1 mg/mL |

The subjects enrolled in the clinical trial were healthy adults, between 50-64 years of age. The mean age was 55.3 years and 72.5% were female. Four groups of subjects (n=8) were vaccinated as follows: 1) 50 microliters of low peptide oil-based formulation on study days 0 and 56; 2) 50 microliters of low peptide alum-based formulation on study day 0 followed by 50 microliters of saline placebo on study day 56; 3) 50 microliters of high peptide oil-based formulation on study days 0 and 56; and 4) 50 microliters of high peptide alum-based formulation on study day 0 followed by 50 microliters of saline placebo on study day 56. A 5$^{th}$ group of subjects (n=8) received 50 microliter dose volume of saline placebo (0.9% sodium chloride) on study days 0 and 56.

The inclusion of comparator groups (placebo control and RSV(A)-Alum) allowed for the estimation of the attributable risk of adverse events. Study holding rules and a safety evaluation by a Safety Review Committee (SRC) were in place.

Example 1—Safety and Reactogenicity

Safety was monitored and measured by solicited and unsolicited adverse events. Events were recorded daily for 1 week following the first administration on study day 0 and the second administration on study day 56.

There were no serious adverse event reports. The most common solicited local adverse event reported was injection site pain. There were no reports of local redness or swelling. Importantly, no increase in injection site pain was observed with the delivery of the booster dose of the oil-based composition.

The most common solicited systemic adverse events reported were drowsiness, nausea, diarrhea and muscle aches. For total unsolicited adverse events, there were no serious adverse events reported and all other events recovered or resolved.

Overall, the results indicate that the low dose volume of the oil-based and alum-based formulations had an acceptable safety profile and there were no serious safety concerns.

Example 2—Immunogenicity

The immunogenicity of the vaccines was monitored for all subjects in the clinical trial by blood serum collection at regular intervals in the study. Antibodies towards the RSV SHeA antigen were detected by enzyme-linked immunosorbent assay (ELISA).

Briefly, 96-well plates were coated with the RSV SHe A peptide dimer as used in the clinical vaccine at 1 microgram per milliliter in carbonate buffer, pH 9.0 for 18-21 hours at 4° C. Plates were then washed with phosphate buffered saline with 0.05% tween (PBS-T) and blocked with assay diluent (ChonBlock, Chondrex) for 1 hour at room temperature. Serial dilutions of the serum were prepared in assay diluent and added to the plate after washing with PBS-T. Each plate tested study day 0 serum in 5 replicates and other time points in triplicate. The plate was incubated at room temperature for 2.5-3 hours then washed with PBS-T. A peroxidase-labeled anti-human IgG was added to the wells and the plate was incubated at room temperature for 1 hour then washed with PBS-T and PBS. The enzyme conjugate TMB microwell peroxdisase substrate system (KPL) was added to the well and allowed to develop at room temperature for up to 4 minutes, followed by TMB stop solution (KPL). The optical density of the wells was read on an ASYS Expert Plus Microplate Reader at 450 nm. An OD cutoff was calculated using the study day 0 OD following the method of Frey A. et al. (Journal of Immunological Methods, 1998, 221:35-41). Calculated titers represent the highest dilution at which an increase in OD is detected relative to the cutoff. Titers were presented as log 10 values of the reciprocal endpoint dilution. The limit of detection for this assay was 1/100 dilution, responses below this limit were reported as log 10=0.

Figure 1:
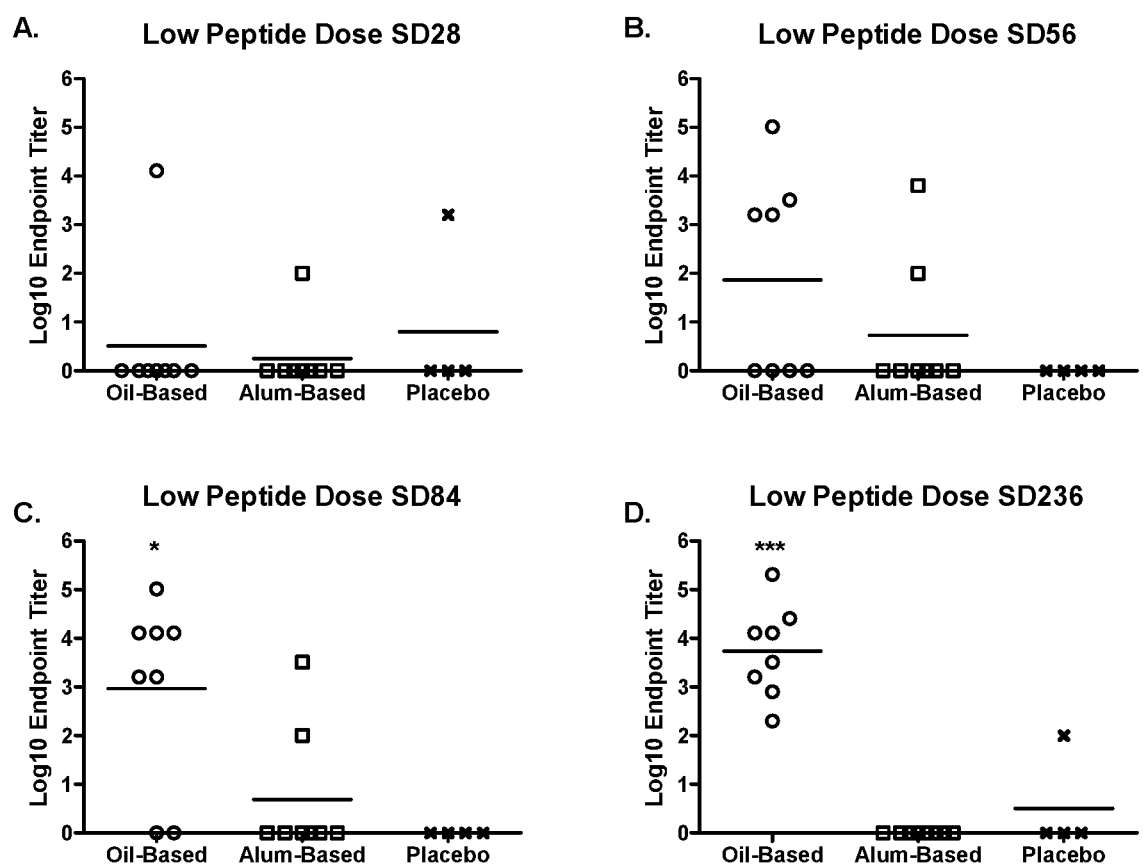
FIG. 1 shows the levels of antibodies towards RSV SHe A peptide antigen detected in serum from subjects in the low peptide groups. Shown are results for study days 28 (A), 56 (B), 84 (C), and 236 (D). Subjects in the oil-based group received two vaccinations on study day 0 and 56. Subjects in the alum-based group received one vaccination on study day 0 and a placebo on study day 56. Subjects in the placebo group received placebo injections on study days 0 and 56. Results below the limit of detection are reported as log 10=0. Data are shown for each individual subject (n=4-8), bar indicates average. Statistical significance calculated by student's t test comparing the oil-based formulation to the alum-based formulation: *p<0.05, ***p<0.001.
Figure 2:
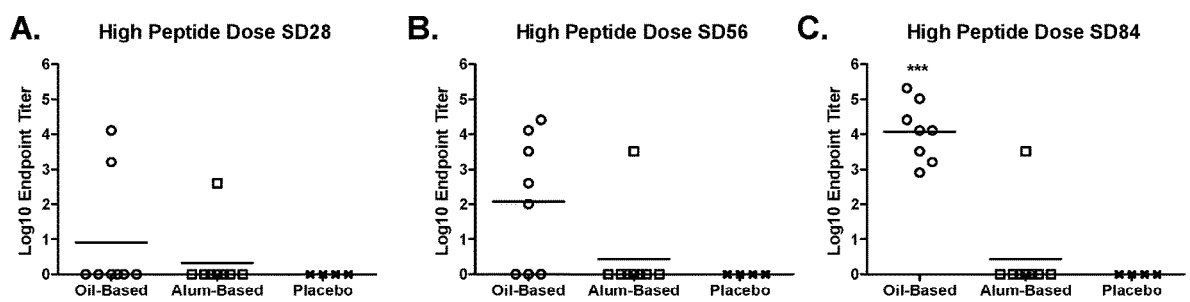
FIG. 2 shows the levels of antibodies towards RSV SHe A peptide antigen detected in serum from subjects in the high peptide groups. Shown are results for study days 28

The endpoint titers for the subjects that received low peptide vaccines are shown in FIG. 1. The endpoint titers for the subjects that received high peptide vaccines are shown in FIG. 2. Table 1 summarizes the endpoint titers for the groups that were vaccinated with low or high peptide oil and alum-based formulations.

TABLE 1

Average endpoint titers with SEM for subjects in the oil-based or alum-based vaccine groups

| Group | N, total | N, above detection limit | Study Day | Average Endpoint Titer | Average Log10 Endpoint Titer |
|---|---|---|---|---|---|
| Low peptide Oil-based formulation | 8 | 1 | 28 | 1601 +/− 1508 | 0.51 +/− 0.51 |
| | 8 | 4 | 56 | 13601 +/− 12692 | 1.87 +/− 0.73 |
| | 8 | 6 | 84 | 18000 +/− 12240 | 2.97 +/− 0.68 |
| | 8 | 8 | 236 | 32725 +/− 24775 | 3.73 +/− 0.34 |
| Low peptide Alum-based formulation | 8 | 1 | 28 | 13 +/− 12 | 0.25 +/− 0.25 |
| | 8 | 2 | 56 | 813 +/− 798 | 0.73 +/− 0.50 |
| | 8 | 2 | 84 | 413 +/− 398 | 0.69 +/− 0.47 |
| | 8 | 0 | 236 | 1 +/− 0 | 0.00 +/− 0.00 |
| High peptide Oil-based formulation | 8 | 2 | 28 | 1801 +/− 1584 | 0.91 +/− 0.60 |
| | 8 | 5 | 56 | 5263 +/− 3295 | 2.08 +/− 0.67 |
| | 8 | 8 | 84 | 45500 +/− 25657 | 4.07 +/− 0.30 |
| High peptide Alum-based formulation | 8 | 1 | 28 | 51 +/− 50 | 0.33 +/− 0.33 |
| | 8 | 1 | 56 | 401 +/− 400 | 0.44 +/− 0.44 |
| | 8 | 1 | 84 | 401 +/− 400 | 0.44 +/− 0.44 |

On study day 56 all groups had received a single immunization. The average endpoint titer of subjects in the low peptide oil-based formulation was 1.87 on study day 56 (4 of 8 subjects with titers above the limit of detection). The average log 10 endpoint titer of subjects in the low peptide alum-based formulation was 0.73 on study day 56 (2 of 8 subjects with titers above the limit of detection). The average log 10 endpoint titer of subjects in the high peptide oil-based formulation was 2.08 on study day 56 (5 of 8 subjects with titers above the limit of detection). The average log 10 endpoint titer of subjects in the high peptide alum-based formulation was 0.44 on study day 56 (1 of 8 subjects with titers above the limit of detection). The average log 10 endpoint titer of subjects in the placebo groups (pooled from each arm of the study) on study day 56 was 0 (0 of 8 subjects with titers above the limit of detection).

These results show that on study day 56, after a single immunization, a low dose volume of the oil-based formulation is significantly more efficient at generating an immune response than a low dose volume of an alum-based formulation each containing the same amount of peptide antigen. The antibody titers induced by the oil-based formulation persisted until at least study day 236 in the group that received the low dose peptide and until at least study day 84 in the group that received the high dose peptide.

Example 3—RSV SHe A and RSV SHe B Titer Comparisons

Pathogen free, female CD1 mice, 6-8 weeks of age were obtained from Charles River Laboratories (St. Constant QC, Canada) and were housed according to institutional guidelines with water and food ad libitum under filter controlled air circulation.

The RSV SHe A peptide antigen dimer (NKLC-EYNVFHNKTFELPRARVNT; SEQ ID NO: 1) and SHe B peptide antigen monomer (NKLSEHKTFSNKTLEQGQMYQINT; SEQ ID NO: 2) were purchased from PolyPeptide Group (San Diego, USA). The RSV SHe A peptide antigen was dimerized by heating at 37° C. overnight in a mixture of water/DMSO/acetic acid. Vaccines for this study contained the RSV SHe A peptide antigen dimer and RSV SHe peptide antigen monomer at 0.5 micrograms per milliliter. The non-adjuvanted oil-based vaccine contained synthetic 1,2-dioleoyl-sn-glycero-3-phosphocholine lipid at 120 milligrams per milliliter (DOPC; Lipoid, GmbH, Germany) and cholesterol at 12 milligrams per milliliter (Lipoid, GmbH, Germany). The vaccine was delivered in ISA 51VG oil (SEPPIC, France). The adjuvanted oil-based vaccine also contained lipopeptide adjuvant at 0.04 milligrams per milliliter (PAM3Cys-Ser-(Lys)4; SEQ ID NO: 3; PolyPeptide, San Diego, USA). The aqueous-based vaccine contained peptide antigen only at 0.5 milligrams per milliliter and was delivered in 10 millimolar sodium acetate pH 7.0 buffer.

Groups of mice (n=8) received two intramuscular vaccinations of a 50 microliter dose volume of each of the three vaccines on study days 0 and 28. Mice were bled at regular intervals to collect serum and immune responses assessed by enzyme linked immunosorbent assay (ELISA) to detect anti-RSV SHe A or RSV SHe B antibodies.

Briefly, a 96-well microtiter plate was coated with RSV SHe A or RSV SHe B antigen (1 microgram per milliliter) overnight at 4 degrees Celsius, blocked with 3% gelatin for 30 minutes at 37 degrees Celsius, then incubated overnight at 4 degrees Celsius with serial dilutions of sera. A secondary antibody (protein G conjugated to alkaline phosphatase, EMD Chemicals, Gibbstown, N.J., USA) was then added to each well at a 1:500 dilution for one hour at 37 degrees Celsius. Following a 60 minute incubation with a solution containing 1 milligram per milliliter 4-nitrophenyl phosphate disodium salt hexahydrate (Sigma-Aldrich Chemie GmbH, Switzerland), the 405 nanometer absorbance of each well was measured using a microtiter plate reader (ASYS Hitech GmbH, Austria). End point titers were calculated as described in Frey A et al. (Journal of Immunological Methods, 1998, 221:35-41). Calculated titers represent the highest dilution at which a statistically significant increase in absorbance was observed in serum samples from immunized mice versus serum samples from naïve, non-immunized mice. Titers are presented as log 10 values of the reciprocal endpoint dilution.

Endpoint titers for RSV SHe A and RSV SHe B peptide antigens are presented in FIG. 3 and summarized in Tables 2 and 3.

TABLE 2

| Average log10endpoint titers +/− SEM | | | | | | |
|---|---|---|---|---|---|---|
| Group | Antigen | Week 4 | Week 8 | Week 12 | Week 16 | Week 20 |
| Non-Adjuvanted oil-based | SHe A | 4.35 +/− 0.58 | 5.41 +/− 0.66 | 5.41 +/− 0.84 | 5.45 +/− 0.75 | 5.59 +/− 0.75 |
| | SHe B | 3.75 +/− 0.51 | 4.13 +/− 0.60 | 3.64 +/− 0.67 | 4.05 +/− 0.64 | 4.02 +/− 0.75 |
| Adjuvanted oil-based | SHe A | 4.66 +/− 0.62 | 5.63 +/− 0.55 | 6.27 +/− 0.78 | 5.80 +/− 0.67 | 5.58 +/− 0.67 |
| | SHe B | 4.20 +/− 0.79 | 3.98 +/− 0.42 | 4.32 +/− 0.64 | 4.08 +/− 0.52 | 3.90 +/− 0.49 |
| Alum-based | SHe A | 3.60 +/− 0.43 | 4.47 +/− 0.49 | 4.77 +/− 0.25 | 4.43 +/− 0.48 | 4.73 +/− 0.57 |
| | SHe B | 3.04 +/− 0.41 | 3.19 +/− 0.48 | 3.30 +/− 0.39 | 3.19 +/− 0.60 | 3.11 +/− 0.48 |

TABLE 3

| Average endpoint titers +/− SEM | | | | | | |
|---|---|---|---|---|---|---|
| Group | Antigen | Week 4 | Week 8 | Week 12 | Week 16 | Week 20 |
| Non-Adjuvanted oil-based | SHe A | 41250 +/− 14981 | 449000 +/− 134210 | 608500 +/− 235278 | 658000 +/− 244967 | 994000 +/− 497973 |
| | SHe B | 9875 +/− 3801 | 28500 +/− 14603 | 19500 +/− 15596 | 29500 +/− 15797 | 44500 +/− 31096 |
| Adjuvanted oil-based | SHe A | 96000 +/− 37615 | 708000 +/− 229040 | 3716000 +/− 1091699 | 1138286 +/− 341228 | 772571 +/− 275843 |
| | SHe B | 51750 +/− 22375 | 15500 +/− 7149 | 46250 +/− 19084 | 20285 +/− 8216 | 12571 +/− 4110 |
| Alum-based | SHe A | 5875 +/− 1817 | 56000 +/− 29277 | 66000 +/− 10664 | 41500 +/− 13937 | 94000 +/− 29655 |
| | SHe B | 1625 +/− 549 | 3188 +/− 1871 | 3000 +/− 1102 | 3750 +/− 1966 | 2250 +/− 931 |

The adjuvanted oil-based formulation induced significantly higher titers to both RSV SHe A (p<0.01) and RSV SHe B (p<0.001) peptide antigens compared to the alum-based formulation. The non-adjuvanted oil-based formulation induced significantly higher titers ($p<0.001$) to the SHe B peptide antigen compared to the alum-based formulation. The non-adjuvanted oil-based formulation induced higher titers to the SHe A peptide antigen than the aqueous-based formulation, but was not statistically significant. These results demonstrate that the adjuvanted oil-based formulations containing the RSV SHe A or RSV SHe B peptide antigen can effectively induce an antibody response that was significantly stronger than an aqueous-based vaccine. These results also demonstrate that the oil-based formulation induces a stronger immune response over the aqueous-based vaccine to multiple peptides.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

REFERENCES

1) Agger, E. M.; Rosenkrands, I.; Olsen, A. W.; Hatch, G.; Williams, A.; Kritsch, C.; Lingnau, K.; von Gabain, A.; Andersen, C. S.; Korsholm, K. S.; Andersen, P. (2006) Protective immunity to tuberculosis with Ag85B-ESAT-6 in a synthetic cationic adjuvant system IC31, *Vaccine* 24(26), 5452-5460.
2) Alexopoulou, L.; Holt, A. C.; Medzhitov, R.; Flavell, R. A. (2001) Recognition of double-stranded RNA and activation of NF-$_{\kappa}$B by Toll-like receptor 3, *Nature* 413 (6857), 732-738.
3) Altschul, S. F.; Gish, W.; Miller, W.; Myers, E. W.; Lipman, D. J. (1990) Basic local alignment search tool, *J. Mol. Biol.* 215(3), 403-410.
4) Altschul, S. F.; Madden, T. L.; Schaffer, A. A.; Zhang, J.; Zhang, Z.; Miller, W.; Lipman, D. J. (1997) Gapped BLAST and PSI-BLAST: a new generation of protein database search programs, *Nucleic Acids Res* 25, 3389-3402
5) Anderson, R.; Huang, Y.; Langley, J. M. (2010) Prospects for defined epitope vaccines for respiratory syncytial virus, *Future Microbiol* 5(4), 585-602.
6) Awasthi, A.; Mehrotra, S.; Bhakuni, V.; Dutta, G. P.; Levy, H. B.; Maheshwari, R. K(1997) Poly ICLC enhances the antimalarial activity of chloroquine against multidrug-resistant *Plasmodium* yoeliinigeriensis in mice, *J. Interferon Cytokine Res.* 17(7), 419-423.
7) Banga, A. K. (1995) Therapeutic Peptides and Proteins, Formulation, Processing and Delivery Systems, Lancaster, Pa.: Technomic Publishing Co.
8) Bever, C. T. Jr.; Salazar, A. M.; Neely, E.; Ferraraccio, B. E.; Rose, J. W.; McFarland H. F.; Levy, H. B.; McFarlin, D. E. (1986) Preliminary trial of poly ICLC in chronic progressive multiple sclerosis, *Neurology* 36(4), 494-498.
9) Bobst, A. M.; Langemeier, P. W.; Torrence, P. F.; De Clercq, E. (1981) Interferon Induction by Poly(inosinic acid) Poly(cytidylic acid) Segmented by Spin-Labels, *Biochemistry* 20(16), 4798-4803.
10) Brewer, K. D.; Lake, K.; Pelot, N.; Stanford, M. M.; DeBay, D. R.; Penwell, A.; Weir, G. M.; Karkada, M.; Mansour, M.; Bowen, C. V. (2014) Clearance of depot vaccine SPIO-labeled antigen and substrate visualized using MRI, *Vaccine* 32(51), 6956-6962.
11) Caruthers, M. H.; Beaucage, S. L.; Efcavitch, J. W.; Fisher, E. F.; Matteucci, M. D.; Stabinsky, Y. (1980) New chemical methods for synthesizing polynucleotides, *Nucleic Acids Res. Symp. Ser.* (7), 215-223.
12) Celis, E.; Ou, D.; Otvos, L. Jr. (1988) Recognition of hepatitis B surface antigen by human T lymphocytes. Proliferative and cytotoxic responses to a major antigenic determinant defined by synthetic peptides, *J. Immunol.* 140, 1808-1815.
13) Chanock, R; Finberg L. (1957) Recovery from infants with respiratory illness of a virus related to chimpanzee coryza agent (CCA). II. Epidemiologic aspects of infection in infants and young children, *Am J Hyg.*66(3), 291-300.
14) Chanock, R.; Roizman B.; Myers, R. (2008)Recovery from infants with respiratory illness of a virus related to chimpanzee coryza agent (CCA). II. Epidemiologic aspects of infection in infants and young children, *Am J Hyg.*66(3), 281-90.
15) Chirigos, M. A.; Schlick, E.; Ruffmann, R.; Budzynski, W.; Sinibaldi, P.; Gruys, E. (1985) Pharmacokinetic and therapeutic activity of polyinosinic-polycytidylic acid stabilized with poly-L-lysine in carboxymethylcellulose [poly(I,C)-LC], *J. Biol. Response Mod.* 4(6), 621-627.
16) Chong, P.; Zobrist, G.; Sia, C.; Loosmore, S.; Klein, M. (1992) Identification of T- and B-cell epitopes of the S2 and S3 subunits of pertussis toxin by use of synthetic peptides, *Infect Immun.* 60, 4640-4647.
17) Collins, P. L.; Olmsted, R. A.; Johnson, P. R. (1990) The small hydrophobic protein of human respiratory syncytial virus: comparison between antigenic subgroups A and B, *J Gen Virol.* 71(7), 1571-6.
18) Cui, Z.; Qiu, F. (2006) Synthetic double-stranded RNA poly(I:C) as a potent peptide vaccine adjuvant: therapeutic activity against human cervical cancer in a rodent model, *Cancer Immunol. Immunother.* 55(10), 1267-1279.
19) deClercq, E.; Hattori, M.; Ikehara, M. (1975) Antiviral activity of polynucleotides: copolymers of inosinic acid and N2-dimethylguanylic of 2-methylthioinosinic acid, *Nucleic Acids Res.* 2(1), 121-129.
20) de Clercq, E.; Torrence, P. F.; Stollar, B. D.; Hobbs, J.; Fukui, T.; Kakiuchi, N.; Ikehara, M. (1978) Interferon induction by a 2'-modified double-helical RNA, poly(2'-azido-2'-deoxyinosinic acid). polycytidylic acid, *Eur. J. Biochem.* 88(2), 341-349.
21) Demotz, S.; Lanzavecchia, A.; Eisel, U.; Niemann, H.; Widmann, C.; Corradin, G. P. (1989) Delineation of several DR-restricted epitopes in tetanus toxin, *J. Immunol.* 142, 394-402.
22) Diethelm-Okita, B. M.; Okita, D. K.; Banaszak, L.; Conti-Fine, B. M. (2000) Universal epitopes for human CD4+ cells on tetanus and diphtheria toxins, *J. Infect. Dis.* 181, 1001-1009.
23) Dong, L. W.; Kong, X. N.; Yan, H. X.; Yu, L. X.; Chen, L.; Yang, W.; Liu, Q.; Huang, D. D.; Wu, M. C.; Wang, H. Y. (2008) Signal regulatory protein alpha negatively regulates both TLR3 and cytoplasmic pathways in type I interferon induction, *Mol. Immunol.* 45(11), 3025-3035.
24) Droller, M. J. (1987) Immunotherapy of metastatic renal cell carcinoma with polyinosinic-polycytidylic acid, *J. Urol.* 137(2), 202-206.
25) Durie, B. G.; Levy, H. B.; Voakes, J.; Jett, J. R.; Levine, A. S. (1985) Poly(I,C)-LC as an interferon inducer in refractory multiple myeloma, *J. Biol. Response Mod.* 4(5), 518-524.
26) Frezard, F. (1999) Liposomes: from biophysics to the design of peptide vaccines, *Braz. J. Med. Bio. Res.* 32, 181-189.
27) Frey, A.; Di Canzio, J.; Zurakowski, D. (1998) A statistically defined endpoint titer determination method for immunoassays, *Journal of Immunological Methods* 221:35-41.
28) Fujimura, T.; Nakagawa, S.; Ohtani, T.; Ito, Y.; Aiba, S. (2006) Inhibitory effect of the polyinosinic-polycytidylic 28) acid/cationic liposome on the progression of murine B16F10 melanoma, *Eur. J. Immunol.* 36(12), 3371-3380.

29) Fukui, T.; Kakiuchi, N.; Ikehara, M. (1977) Polynucleotides. XLV Synthesis and properties of poly(2'-azido-2'-deoxyinosinic acid), *Nucleic Acids Res.* 4(8), 2629-2639.

30) Gowen, B. B.; Wong, M. H.; Jung, K. H.; Sanders, A. B.; Mitchell, W. M.; Alexopoulou, L.; Flavell, R. A.; Sidwell, R. W. (2007) TLR3 is essential for the induction of protective immunity against Punta Toro Virus infection by the double-stranded RNA (dsRNA), poly(I:C12U), but not Poly(I:C): differential recognition of synthetic dsRNA molecules, *J. Immunol.* 178(8), 5200-5208.

31) Gregoriadis G. (1990) Immunological adjuvants: a role for liposomes, Immunol. Today 11, 89-97.

32) Greene, J. J.; Alderfer, J. L.; Tazawa, I.; Tazawa, S.; Ts'o, P. O.; O'Malley, J. A.; Carter, W. A. (1978) Interferon induction and its dependence on the primary and secondary structure of poly(inosinic acid).poly(cytidylic acid), *Biochemistry* 17(20), 4214-4220.

33) Guschlbauer, W.; Blandin, M.; Drocourt, J. L.; Thang, M. N. (1977) Poly-2'-deoxy-2'-fluoro-cytidylic acid: enzymatic synthesis, spectroscopic characterization and interaction with poly-inosinic acid, *Nucleic Acids Res.* 4(6), 1933-1943.

34) Hendrix, C. W.; Margolick, J. B.; Petty, B. G.; Markham, R. B.; Nerhood, L.; Farzadegan, H.; Ts'o, P. O.; Lietman, P. S. (1993) Biologic effects after a single dose of poly (I):poly(C12U) in healthy volunteers, *Antimicrob. Agents Chemother.* 37(3), 429-435.

35) Horn, T.; Vasser, M. P.; Struble, M. E.; Crea, R. (1980) Synthesis of oligonucleotides on cellulose. Part II: Design and synthetic strategy to the synthesis of 22 oligodeoxynucleotides coding for gastric inhibitory polypeptide (GIP), *Nucleic Acids Symp. Ser.* (7), 225-232.

36) Houston, W. E.; Crabbs, C. L.; Stephen, E. L.; Levy, H. B. (1976) Modified polyriboinosinic-polyribocytidylicacid, an immunological adjuvant, *Infect. Immun.* 14(1), 318-319.

37) Ichinohe, T.; Tamura, S.; Kawaguchi, A.; Ninomiya, A.; Imai, M.; Itamura, S.; Odagiri, T.; Tashiro, M.; Takahashi, H.; Sawa, H.; Mitchell, W. M.; Strayer, D. R.; Carter, W. A.; Chiba, J.; Kurata, T.; Sata, T.; Hasegawa, H. (2007) Cross-protection against H5N1 influenza virus infection is afforded by intranasal inoculation with seasonal trivalent inactivated influenza vaccine, *J. Infect. Dis.* 196(9), 1313-1320.

38) Johnston, M. I.; Stollar, B. D.; Torrence, P. F.; Witkop, B. (1975) Structural features of double-stranded polyribonucleotides required for immunological specificity and interferon induction, *Proc. Natl. Acad. Sci. U.S.A* 72(11), 4564-4568.

39) Kamath, A. T.; Valenti, M. P.; Rochat, A. F.; Agger, E. M.; Lingnau, K.; von Gabain, A.; Andersen, P.; Lambert, P. H.; Siegrist, C. A. (2008) Protective anti-mycobacterial T cell responses through exquisite in vivo activation of vaccine-targeted dendritic cells, *Eur. J. Immunol.* 38(5), 1247-1256.

40) Karron R A, *Respiratory syncytial virus and parainfluenza virus vaccines*, in *Vaccines*, Plotkin S. A.; Orenstein W. A.; and Offit, P. A., Editors. 2013, Elsevier Saunders, 1146-1153.

41) Kawaoka, Y.; Yamnikova, S.; Chambers, T. M.; Lvov, D. K.; Webster, R. G. (1990) Molecular characterization of a new hemagglutinin, subtype H14, of influenza A virus, *Virology* 179(2), 759-767

42) Kende, M.; Lupton, H. W.; Rill, W. L.; Gibbs, P.; Levy, H. B.; Canonico, P. G. (1987) Ranking of Prophylactic Efficacy of Poly(ICLC) against Rift Valley Fever Virus Infection in Mice by Incremental Relative Risk of Death, *Antimicrob. Agents Chemother.* 31(8), 1194-1198.

43) Khanna, N.; Widmer, A. F.; Decker, M.; Steffen, I., Halter, J.; Heim, D.; Weisser, M.; Gratwohl, A.; Fluckiger, U.; Hirsch, H. H. (2008) Respiratory syncytial virus infection in patients with hematological diseases: single-center study and review of the literature, *Clin Infect Dis.* 46(3), 402-12.

44) Kreuter, J., ed. (1994), Colloidal Drug Delivery Systems, Vol. 66, Marcel Dekker, Inc.

45) Krown, S. E.; Kerr, D.; Stewart, W. E. 2nd; Field, A. K.; Oettgen, H. F. (1985) Phase I trials of poly(I,C) complexes in advanced cancer, *J. Biol. Response Mod.* 4(6), 640-649.

46) Langley, J. M.; LeBlanc, J. C.; Smith, B.; Wang, E. E. (2003) Increasing incidence of hospitalization for bronchiolitis among Canadian children, 1980-2000, *J Infect Dis.* 188(11), 1764-7.

47) Levy, H. B; Lvovsky, E. (1978) Topical treatment of vaccinia virus infection with an interferon inducer in rabbits, *J. Infect. Dis.* 137(1), 78-81.

48) Levy, H. B. (1985) Historical overview of the use of polynucleotides in cancer, *J. Biol. Response Mod.* 4(5), 475-480.

49) Llopiz, D.; Dotor, J.; Zabaleta, A.; Lasarte, J. J.; Prieto, J.; Borrás-Cuesta, F.; Sarobe, P. (2008) Combined immunization with adjuvant molecules poly(I.C) and anti-CD40 plus a tumor antigen has potent prophylactic and therapeutic antitumor effects, *Cancer Immunol. Immunother.* 57(1), 19-29.

50) Merrifield, B. (1997) Concept and early development of solid-phase peptide synthesis, *Methods Enzymol.* 289, 3-13.

51) Moghaddam, A.; Olszewska, W.; Wang, B.; Tregoning, J. S.; Helson, R.; Sattentau, Q. J.; Openshaw, P. J. (2006) A potential molecular mechanism for hypersensitivity caused by formalin-inactivated vaccines, *Nat Med.* 12(8), 905-7.

52) Moyle, P. M.; Toth. I. (2008) Self-adjuvanting lipopeptide vaccines, *Curr. Med. Chem.* 15(5), 506-516.

53) Nair, H.; Nokes, D. J.; Gessner, B. D.; Dherani, M.; Madhi, S. A.; Singleton, R. J. et al., (2010) Global burden of acute lower respiratory infections due to respiratory syncytial virus in young children: a systematic review and meta-analysis, *Lancet* 375(9725), 1545-55.

54) Nair, H.; Verma, V. R.; Theodoratou, E.; Zgaga, L.; Huda, T.; Simões, E.A.F.; Wright, P. F.; Rudan, I.; Campbell, H. (2011) An evaluation of the emerging interventions against Respiratory Syncytial Virus (RSV)-associated acute lower respiratory infections in children, *BMC Public Health* 11 Suppl 3, S30.

55) Nakamura, O.; Shitara, N.; Matsutani, M.; Takakura, K.; Machida, H. (1982) Phase I-II trials of poly(ICLC) in malignant brain tumor patients, *J. Interferon. Res.* 2(1), 1-4.

56) Needleman, S. B.; Wunsch, C. D. (1970) A general method applicable to the search for similarities in the amino acid sequence of two proteins, *J. Mol. Biol.* 48(3), 443-453.

57) Padalko, E.; Nuyens, D.; De Palma, A.; Verbeken, E.; Aerts, J. L.; De Clercq, E.; Carmeliet, P.; Neyts, J. (2004) The Interferon Inducer Ampligen[poly(I)-poly($C_{12}U$)] Markedly Protects Mice against Coxsackie B3 Virus-Induced Myocarditis, *Antimicrob. Agents Chemother.* 48(1), 267-274.

58) Pearson, W. R.; Lipman, D. J. (1988) Improved tools for biological sequence comparison, *Proc. Natl. Acad. Sci. U.S.A* 85(8), 2444-2448.

59) Poast, J.; Seidel, H. M.; Hendricks, M. D.; Haslam, J. A.; Levy, H. B.; Baron, S. (2002) Poly I:CLC induction of the interferon system in mice: an initial study of four detection methods, *J. Interferon Cytokine Res.* 22(10), 1035-1040.

60) Puri, S. K.; Dutta, G. P.; Levy, H. B.; Maheshwari, R. K. (1996) Poly ICLC inhibits *Plasmodium* cynomolgi B malaria infection in rhesus monkeys, J. Interferon. *Cytokine Res.* 16(1), 49-52.

61) Remington's Pharmaceutical Sciences, Mack Publishing Company, Easton, Pa., USA 1985

62) Riedl, K.; Riedl, R.; von Gabain, A.; Nagy, E.; Lingnau, K. (2008) The novel adjuvant IC31® strongly improves influenza vaccine-specific cellular and humoral immune responses in young adult and aged mice, *Vaccine* 26(27-28), 3461-3468.

63) Roberge, J. Y.; Beebe, X.; Danishefsky, S. J. (1995) A strategy for a convergent synthesis of N-linked glycopeptides on a solid support, *Science* 269(5221), 202-204.

64) Salazar, A. M.; Levy, H. B.; Ondra, S.; Kende, M.; Scherokman, B.; Brown, D.; Mena, H.; Martin, N.; Schwab, K.; Donovan, D.; Dougherty, D.; Pulliam, M.; Ippolito, M.; Graves, M.; Brown, H.; Ommaya, A. (1996) Long-term treatment of malignant gliomas with intramuscularly administered polyinosinic-polycytidylic acid stabilized with polylysine and carboxymethylcellulose: an open pilot study, *Neurosurgery* 38(6), 1096-1103, discussion at 1103-1104.

65) Salem, M. L.; Kadima, A. N.; Cole, D. J.; Gillanders, W. E. (2005) Defining the antigen-specific T-cell response to vaccination and poly(I:C)/TLR3 signaling: evidence of enhanced primary and memory CD8 T-cell responses and antitumor immunity, *J. Immunother.* 28(3), 220-228.

66) Salem, M. L.; El-Naggar, S. A.; Kadima, A.; Gillanders, W. E.; Cole, D. J. (2006) The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, *Vaccine* 24(24), 5119-5132.

67) Sarma, P. S.; Shiu, G.; Neubauer, R. H.; Baron, S.; Huebner, R. J. (1969) Virus-induced sarcoma of mice: inhibition by a synthetic polyribonucleotide complex, *Proc. Natl. Acad. Sci. U.S.A* 62(4), 1046-1051.

68) Schellack, C.; Prinz, K.; Egyed, A.; Fritz, J. H.; Wittmann, B.; Ginzler, M.; Swatosch, G.; Zauner, W.; Kast, C.; Akira, S.; von Gabain, A.; Buschle, M.; Lingnau, K. (2006) IC31, a novel adjuvant signaling via TLR9, induces potent cellular and humoral immune responses, *Vaccine* 24(26), 5461-5472.

69) Sharon, J; Rynkiewicz M. J.; Lu, Z.; Yang, C. Y. (2014) Discovery of protective B-cell epitopes for development of antimicrobial vaccines and antibody therapeutics, *Immunology* 142(1), 1-23.

70) Slingluff, C. L. Jr.; Yamshchikov, G.; Neese, P.; Galavotti, H.; Eastham, S.; Engelhard, V. H.; Kittlesen, D.; Deacon, D.; Hibbitts, S.; Grosh, W. W.; Petroni, G.; Cohen, R.; Wiernasz, C.; Patterson, J. W.; Conway, B. P.; Ross, W. G. (2001) Phase I trial of a melanoma vaccine with gp100(280-288) peptide and tetanus helper peptide in adjuvant: Immunologic and clinical outcomes, *Clin Cancer Res.* 7, 3012-3024.

71) Sloat, B. R.; Shaker, D. S.; Le, U. M.; Cui, Z. (2008) Nasal immunization with the mixture of PA63, LF, and a PGA conjugate induced strong antibody responses against all three antigens, *FEMS Immunol. Med. Microbiol.* 52(2), 169-179.

72) Smith, T. F.; Waterman, M. S. (1981) Comparison of biosequences, *Adv. Appl. Math.* 2(4), 482-489.

73) So, N. S. Y.; Ostrowski, M. A.; Gray-Owen, S. D. (2012) Vigorous Response of Human Innate Functioning IgM Memory B Cells upon Infection by *Neisseria gonorrhoeae, J. Immunol.* 188(8), 4008-4022.

74) Stephen, E. L.; Sammons, M. L.; Pannier, W. L.; Baron, S.; Spertzel, R. O.; Levy, H. B. (1977) Effect of a nuclease-resistant derivative of polyriboinosinic-polyribocytidylic acid complex on yellow fever in rhesus monkeys (Macacamulatta), *J. Infect. Dis.* 136(1), 122-126.

75) Talmadge, J. E.; Adams, J.; Phillips, H.; Collins, M.; Lenz, B.; Schneider, M.; Chirigos, M. (1985) Immunotherapeutic potential in murine tumor models of polyinosinic-polycytidylic acid and poly-L-lysine solubilized by carboxymethylcellulose, *Cancer Res.* 45(3), 1066-1072.

76) The United States Pharmacopoeia: The National Formulary (USP 24 NF19) published in 1999

77) Theriault, R. L.; Hortobagyi, G. N.; Buzdar, A. U.; Levy, H. B.; Hersh, E. M. (1986) Evaluation of polyinosinic-polycytidylic and poly-L-lysine in metastatic breast cancer, *Cancer Treat. Rep.* 70(11), 1341-1342.

78) Trumpfheller, C.; Caskey, M.; Nchinda, G.; Longhi, M. P.; Mizenina, O.; Huang, Y.; Schlesinger. S. J.; Colonna, M.; Steinman, R. M. (2008) The microbial mimic poly IC induces durable and protective CD4+ T cell immunity together with a dendritic cell targeted vaccine, *Proc. Natl. Acad. Sci. U.S.A* 105(7), 2574-2579.

79) Van Regenmortel, M. H. (2009) What is a B-cell epitope?, *Methods Mol Biol.* 524, 3-20.

80) Walsh, E. E.; Falsey, A. R. (2004) Humoral and mucosal immunity in protection from natural respiratory syncytial virus infection in adults, *J Infect Dis.* 190(2), 373-8.

81) Webster, R. G.; Laver, W. G.; Air, G. M. Antigenic variation among type A influenza viruses, p. 127-168. In: Palese, P. & Kingsbury, D. W., eds. Genetics of influenza viruses. (New York: Springer-Verlag, 1983).

82) Zaks, K.; Jordan, M.; Guth, A.; Sellins, K.; Kedl, R.; Izzo, A.; Bosio, C.; Dow, S. (2006) Efficient immunization and cross-priming by vaccine adjuvants containing TLR3 or TLR9 agonists complexed to cationic liposomes, *J. Immunol.* 176(12), 7335-7345.

83) Yoneyama, M.; Kikuchi, M.; Natsukawa, T.; Shinobu, N.; Imaizumi, T.; Miyagishi, M.; Taira, K.; Akira, S.; Fujita, T. (2004) The RNA helicase RIG-I has an essential function in double-stranded RNA-induced innate antiviral responses, *Nat. Immunol.* 5(7), 730-737.

84) Kametani, Y.; Miyamoto, A.; Tsuda, B.; Tokuda, Y. (2015) B Cell Epitope-Based Vaccination Therapy, *Antibodies* 4(3), 225-239.

85) Zhu, X.; Nishimura, F.; Sasaki, K.; Fujita, M.; Dusak, J. E.; Eguchi, J.; Fellows-Mayle, W.; Storkus, W. J.; Walker, P. R.; Salazar, A. M.; Okada, H. (2007) Toll like receptor-3 ligand poly-ICLC promotes the efficacy of peripheral vaccinations with tumor antigen-derived peptide epitopes in murine CNS tumor models, *J. Transl. Med.* 5(10), 1-15.

The invention claimed is:

1. A method for inducing an antibody immune response in a human subject, comprising administering parenterally to the human subject a low dose volume of a composition comprising:
   between about 5-50 μg of an antigen comprising a B-cell epitope;
   an amphipathic compound; and
   a hydrophobic carrier,
   wherein the low dose volume of the composition is less than 100 μl and induces an antibody immune response to the B-cell epitope in the human subject.

2. A low dose volume of a composition comprising:
   an antigen comprising a B-cell epitope;
   an amphipathic compound; and
   a hydrophobic carrier,
   for inducing an antibody immune response to the B-cell epitope in a human subject, wherein the composition is for administration parenterally and the low dose volume of the composition is less than 100 μl.

3. A kit for inducing an antibody immune response in a human subject, wherein the kit comprises a low dose composition comprising an antigen comprising a B-cell epitope; an amphipathic compound; and a hydrophobic carrier, wherein the composition is for administration parenterally and the low dose volume of the composition is less than 100 μl.

4. The composition of claim 2, wherein the low dose volume is about 50 μl, about 60 μl, about 70 μl, about 80 μl or about 90 μl.

5. The composition of claim 2, wherein the low dose volume is 50 μl.

6. The composition of claim 2, wherein (i) only a single administration of the composition is administered to the human subject, or (ii) only a single priming administration and a single booster administration of the composition is administered to the human subject.

7. The composition of claim 6, wherein:
   the single booster administration is administered to the human subject about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, or more after the single priming administration; or
   the single booster administration is administered to the human subject about 56 days after the single priming administration.

8. The composition of claim 2, wherein the composition:
   induces an antibody immune response that is detectable in the human subject at least as early as 28 days after a first administration of the composition;
   induces an antibody immune response that persists in the human subject for at least 84 days or at least 236 days after a first administration of the composition;
   induces an antibody immune response in at least 75%, at least 80%, at least 85%, at least 90%, at least 95% or at least 100% of the human subjects by day 56, day 84 or day 236 post-administration;
   induces an antibody immune response in 100% of treated human subjects at least by day 84 or day 236 post-administration; and/or
   induces an antibody immune response that is enhanced as compared to the antibody immune response induced in human subjects administered the antigen formulated in an alum composition, wherein the alum composition comprises the antigen, an alum adjuvant, a mineral adjuvant (e.g., Alhyrogel), and an aqueous carrier.

9. The composition of claim 8, wherein the composition induces an antibody immune response that is enhanced as compared to the antibody immune response induced in human subjects administered the alum composition, wherein:
   each of the composition and the alum composition comprise 10 μg of the antigen and the average antigen-specific antibody endpoint titer with the composition is: (i) at least about 123.2 times higher than the alum composition at day 28 post-administration; and/or (ii) at least about 16.7 times higher than the alum composition at day 56;
   each of the composition and the alum composition comprise 25 μg of the antigen and the average antigen-specific antibody endpoint titer for the composition is: (i) at least about 35.3 times higher than the alum composition at day 28 post-administration; and/or (ii) at least about 13.1 times higher than the alum composition at day 56;
   each of the composition and the alum composition comprise 10 μg of the antigen and the percentage of human subjects that have a detectable antigen-specific antibody immune response when treated with the composition is at least about 2.0 times higher than with the alum composition, at day 56 post-administration;
   each of the composition and the alum composition comprise 25 μg of the antigen and the percentage of human subjects that have a detectable antigen-specific antibody immune response when treated with the composition is at least about 5.0 times higher than with the alum composition, at day 56 post-administration; and/or
   the composition has an acceptable safety profile in respect of total solicited systemic adverse events and/or total unsolicited adverse events.

10. The composition of claim 2, wherein the composition further comprises an adjuvant selected from a polyI:C polynucleotide adjuvant, a lipid-based adjuvant, a lipid A mimic or analog thereof, or any combination thereof.

11. The composition of claim 2, wherein the antigen is: a peptide antigen of 5 to 50 amino acids in length or a polynucleotide encoding the peptide antigen; or a synthetic peptide antigen that is naturally weakly immunogenic in the human subject.

12. The composition of claim 2, wherein the antigen comprises or consists of the ectodomain of the small hydrophobic protein (SHe) of a Respiratory Syncytial Virus (RSV), or a fragment thereof.

13. The composition of claim 12, wherein the SHe is derived from a subgroup A human RSV strain or a subgroup B human RSV strain.

14. The composition of claim 2, wherein the antigen comprises or consists of the amino acid sequence NKLCEYNVFHNKTFELPRARVNT (SEQ ID NO 1), an amino acid sequence that is at least 75% identical to SEQ ID NO: 1, or a fragment of SEQ ID NO: 1.

15. The composition of claim 2, wherein the amphipathic compound is a lipid or a lipid mixture; and/or the hydrophobic carrier is an oil or a mixture of oils.

16. The composition of claim 2, wherein the composition comprises:

a peptide comprising the amino acid sequence NKLCEYNVFHNKTFELPRARVNT (SEQ ID NO: 1);

a lipid mixture comprising dioleoyl phosphatidylcholine (DOPC) and cholesterol;

a short synthetic lipopeptide which is $PAM_3Cys$-Ser-$(Lys)_4$ (SEQ ID NO: 3); and Montanide® ISA 51 VG.

17. The composition of claim 2, wherein the composition is water-free or substantially free of water.

18. The composition of claim 2, wherein the composition is suitable for intramuscular injection.

19. The composition of claim 2, wherein the composition is for treatment or prevention of an infectious disease in the human subject.

* * * * *

SEQUENCE LISTING

<160> NUMBER OF SEQ ID NOS: 12

<210> SEQ ID NO 1
<211> LENGTH: 23
<212> TYPE: PRT
<213> ORGANISM: Artificial Sequence
<220> FEATURE:
<223> OTHER INFORMATION: RSV SHe A peptide

<400> SEQUENCE: 1

Asn Lys Leu Cys Glu Tyr Asn Val Phe His Asn Lys Thr Phe Glu Leu
1               5                   10                  15

Pro Arg Ala Arg Val Asn Thr
            20

<210> SEQ ID NO 2
<211> LENGTH: 24
<212> TYPE: PRT
<213> ORGANISM: Artificial Sequence
<220> FEATURE:
<223> OTHER INFORMATION: RSV SHe B peptide

<400> SEQUENCE: 2

Asn Lys Leu Ser Glu His Lys Thr Phe Cys Asn Lys Thr Leu Glu Gln
1               5                   10                  15

Gly Gln Met Tyr Gln Ile Asn Thr
            20

<210> SEQ ID NO 3
<211> LENGTH: 6
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM2 or PAM3

<400> SEQUENCE: 3

Cys Ser Lys Lys Lys Lys
1               5

<210> SEQ ID NO 4
<211> LENGTH: 64
<212> TYPE: PRT
<213> ORGANISM: Artificial Sequence
<220> FEATURE:
<223> OTHER INFORMATION: Human RSV SH Subgroup A

<400> SEQUENCE: 4

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
            20                  25                  30

Ile Ile Ser Ile Met Ile Ala Ile Leu Asn Lys Leu Cys Glu Tyr Asn
        35                  40                  45

Val Phe His Asn Lys Thr Phe Glu Leu Pro Arg Ala Arg Val Asn Thr
    50                  55                  60

<210> SEQ ID NO 5
<211> LENGTH: 65
<212> TYPE: PRT
<213> ORGANISM: Artificial Sequence
<220> FEATURE:

```
<223> OTHER INFORMATION: Human RSV SH Subgroup B

<400> SEQUENCE: 5

Met Gly Asn Thr Ser Ile Thr Ile Glu Phe Thr Ser Lys Phe Trp Pro
1               5                   10                  15

Tyr Phe Thr Leu Ile His Met Ile Leu Thr Leu Ile Ser Leu Leu Ile
                20                  25                  30

Ile Ile Thr Ile Met Ile Ala Ile Leu Asn Lys Leu Ser Glu His Lys
            35                  40                  45

Thr Phe Cys Asn Lys Thr Leu Glu Gln Gly Gln Met Tyr Gln Ile Asn
        50                  55                  60

Thr
65

<210> SEQ ID NO 6
<211> LENGTH: 23
<212> TYPE: PRT
<213> ORGANISM: Artificial Sequence
<220> FEATURE:
<223> OTHER INFORMATION: RSV SHe A peptide variant

<400> SEQUENCE: 6

Asn Lys Leu Ser Glu Tyr Asn Val Phe His Asn Lys Thr Phe Glu Leu
1               5                   10                  15

Pro Arg Ala Arg Val Asn Thr
                20

<210> SEQ ID NO 7
<211> LENGTH: 9
<212> TYPE: PRT
<213> ORGANISM: Artificial Sequence
<220> FEATURE:
<223> OTHER INFORMATION: HPV R9F peptide

<400> SEQUENCE: 7

Arg Ala His Tyr Asn Ile Val Thr Phe
1               5

<210> SEQ ID NO 8
<211> LENGTH: 20
<212> TYPE: DNA
<213> ORGANISM: Artificial Sequence
<220> FEATURE:
<223> OTHER INFORMATION: CpG Oligonucleotide

<400> SEQUENCE: 8
tccatgacgt tcctgacgtt                                           20

<210> SEQ ID NO 9
<211> LENGTH: 26
<212> TYPE: DNA
<213> ORGANISM: Artificial Sequence
<220> FEATURE:
<223> OTHER INFORMATION: PolyI:C polynucleotide
<220> FEATURE:
<221> NAME/KEY: modified_base
<222> LOCATION: (1)..(1)
<223> OTHER INFORMATION: Inosine
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (5)..(5)
<223> OTHER INFORMATION: Inosine
```

-continued

```
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (13)..(13)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (17)..(17)
<223> OTHER INFORMATION: Inosine
<220> FEATURE:
<221> NAME/KEY: modified_base
<222> LOCATION: (19)..(19)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (25)..(25)
<223> OTHER INFORMATION: Inosine

<400> SEQUENCE: 9
ncncncncnc ncncncncnc ncncnc                                          26

<210> SEQ ID NO 10
<211> LENGTH: 16
<212> TYPE: PRT
<213> ORGANISM: Artificial Sequence
<220> FEATURE:
<223> OTHER INFORMATION: Tetanus toxin peptide A16L

<400> SEQUENCE: 10

Ala Gln Tyr Ile Lys Ala Asn Ser Lys Phe Ile Gly Ile Thr Glu Leu
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: T-helper epitope PADRE
<220> FEATURE:
<221> NAME/KEY: MISC_FEATURE
<222> LOCATION: (3)..(3)
<223> OTHER INFORMATION: Xaa may be cyclohexylalanyl

<400> SEQUENCE: 11

Ala Lys Xaa Val Ala Ala Trp Thr Leu Lys Ala Ala Ala
1               5                   10

<210> SEQ ID NO 12
<211> LENGTH: 21
<212> TYPE: PRT
```

```
<213> ORGANISM: Artificial Sequence
<220> FEATURE:
<223> OTHER INFORMATION: Tetanus toxoid peptide F21E

<400> SEQUENCE: 12

Phe Asn Asn Phe Thr Val Ser Phe Trp Leu Arg Val Pro Lys Val Ser
1               5                   10                  15

Ala Ser His Leu Glu
            20
```